(12) United States Patent
Weidner et al.

(10) Patent No.: US 12,714,426 B2
(45) Date of Patent: Aug. 25, 2026

(54) RELOAD COVER FOR SURGICAL STAPLING SYSTEM

(71) Applicant: Applied Medical Resources Corporation, Rancho Santa Margarita, CA (US)

(72) Inventors: Jeffrey Weidner, Rancho Santa Margarita, CA (US); Nicholas Humphreys, Aliso Viejo, CA (US); Timothy M. Hopkins, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 0 days.

(21) Appl. No.: 19/070,171

(22) Filed: Mar. 4, 2025

(65) Prior Publication Data

US 2025/0195068 A1 Jun. 19, 2025

Related U.S. Application Data

(63) Continuation of application No. 18/338,644, filed on Jun. 21, 2023, now Pat. No. 12,285,167, which is a (Continued)

(51) Int. Cl.
*A61B 17/072* (2006.01)
*A61B 17/00* (2006.01)

(52) U.S. Cl.
CPC .................. *A61B 17/07207* (2013.01); *A61B 2017/00477* (2013.01); *A61B 2017/0053* (2013.01); *A61B 2017/07271* (2013.01)

(58) Field of Classification Search
CPC ........... A61B 17/072; A61B 17/07207; A61B 17/07271; A61B 2017/07214
See application file for complete search history.

(56) References Cited

U.S. PATENT DOCUMENTS 2,073,960 A 3/1937 Crosby
2,140,593 A 12/1938 Pankonin (Continued)

FOREIGN PATENT DOCUMENTS

EP 0 251 444 A1 1/1988
EP 0 492 283 A1 7/1992

(Continued)

OTHER PUBLICATIONS

European Patent Office, International Search Report and Written Opinion for International Application No. PCT/US2014/028211, entitled "Surgical Stapler with Partial Pockets," mailed Sep. 8, 2014, 17 pgs.

(Continued)

*Primary Examiner* — Gloria R Weeks
(74) *Attorney, Agent, or Firm* — John F. Heal

(57) ABSTRACT

Surgical stapler systems can include a jaw assembly with one jaw defining a reload support capable of receiving and firing multiple disposable reload cartridges in a single surgical procedure. The reload cartridge can be protected by a reload cover engageable therewith. The reload cover can include snap features configured to prevent manual removal of the reload cover from the reload cartridge before proper positioning and installation in the reload support. The reload cover can desirably maintain a plurality of staples within staple pockets in the reload cartridge and can maintain a staple deployment mechanism in an unfired position.

15 Claims, 7 Drawing Sheets

Related U.S. Application Data continuation of application No. 16/833,288, filed on Mar. 27, 2020, now Pat. No. 11,717,293.

(60) Provisional application No. 62/826,194, filed on Mar. 29, 2019.

(56) References Cited

U.S. PATENT DOCUMENTS 2,351,608 A 6/1944 Greenwood
2,487,565 A 11/1949 Leber et al.
2,641,154 A 6/1953 Heller
3,076,373 A 2/1963 Matthews
3,077,812 A 2/1963 Dietrich
3,080,564 A 3/1963 Strekopitov et al.
3,203,220 A 8/1965 Kaepernik
3,252,643 A 5/1966 Strekopitov et al.
3,273,562 A 9/1966 Brown
3,373,646 A 3/1968 Ehlert
3,459,187 A 8/1969 Pallotta
3,494,533 A 2/1970 Green et al.
3,662,939 A 5/1972 Bryan
3,675,688 A 7/1972 Bryan et al.
3,692,224 A 9/1972 Astafiev et al.
4,261,244 A 4/1981 Becht et al.
4,281,785 A 8/1981 Brooks
4,304,236 A 12/1981 Conta et al.
4,312,363 A 1/1982 Rothfuss et al.
4,317,451 A 3/1982 Cerwin et al.
4,407,286 A 10/1983 Noiles et al.
4,434,796 A 3/1984 Karapetian et al.
4,442,964 A 4/1984 Becht
4,454,875 A 6/1984 Pratt et al.
4,522,327 A 6/1985 Korthoff et al.
4,527,724 A 7/1985 Chow et al.
4,589,582 A 5/1986 Bilotti
4,591,085 A 5/1986 Di Giovanni
4,606,344 A 8/1986 Di Giovanni
4,608,981 A 9/1986 Rothfuss et al.
4,610,383 A 9/1986 Rothfuss et al.
4,728,020 A 3/1988 Green et al.
4,805,823 A 2/1989 Rothfuss
4,892,244 A 1/1990 Fox et al.
4,923,350 A 5/1990 Hinksman et al.
4,941,623 A 7/1990 Pruitt
4,955,959 A 9/1990 Tompkins et al.
4,978,049 A 12/1990 Green
5,031,814 A 7/1991 Tompkins et al.
5,065,929 A 11/1991 Schulze et al.
5,071,052 A 12/1991 Rodak et al.
5,106,008 A 4/1992 Tompkins et al.
5,116,349 A 5/1992 Aranyi
5,129,570 A 7/1992 Schulze et al.
5,180,092 A 1/1993 Crainich
5,201,746 A 4/1993 Shichman
5,221,036 A 6/1993 Takase
5,236,440 A 8/1993 Hlavacek
5,240,163 A 8/1993 Stein et al.
RE34,519 E 1/1994 Fox et al.
5,275,323 A 1/1994 Schulze et al.
5,289,963 A 3/1994 McGarry et al.
D347,474 S 5/1994 Olson
5,307,976 A 5/1994 Olson et al.
5,308,576 A 5/1994 Green et al.
5,326,013 A 7/1994 Green et al.
5,350,400 A 9/1994 Esposito et al.
5,360,305 A 11/1994 Kerrigan
5,364,002 A 11/1994 Green et al.
5,366,479 A 11/1994 McGarry et al.
5,381,943 A 1/1995 Allen et al.
5,389,098 A 2/1995 Tsuruta et al.
5,395,034 A 3/1995 Allen et al.
5,397,046 A 3/1995 Savage et al.
5,413,267 A 5/1995 Solyntjes et al.
5,415,334 A 5/1995 Williamson, IV et al.
5,415,335 A 5/1995 Knodell, Jr.
5,439,155 A 8/1995 Viola
5,439,479 A 8/1995 Shichman et al.
5,445,304 A 8/1995 Plyley et al.
5,447,265 A 9/1995 Vidal et al.
5,452,836 A 9/1995 Huitema et al.
5,456,401 A 10/1995 Green et al.
5,458,279 A 10/1995 Plyley
5,462,215 A 10/1995 Viola et al.
5,464,144 A 11/1995 Guy et al.
5,465,895 A 11/1995 Knodel et al.
5,470,006 A 11/1995 Rodak
5,470,007 A 11/1995 Plyley et al.
5,470,008 A 11/1995 Rodak
5,470,009 A 11/1995 Rodak
5,472,132 A 12/1995 Savage et al.
5,480,089 A 1/1996 Blewett
5,485,952 A 1/1996 Fontayne
5,487,500 A 1/1996 Knodel et al.
5,489,058 A 2/1996 Plyley
5,497,933 A 3/1996 DeFonzo et al.
5,507,426 A 4/1996 Young et al.
5,507,773 A 4/1996 Huitema et al.
5,509,596 A 4/1996 Green et al.
5,509,920 A 4/1996 Phillips et al.
5,529,235 A 6/1996 Boiarski et al.
5,547,117 A 8/1996 Hamblin et al.
5,553,765 A 9/1996 Knodel et al.
5,554,164 A 9/1996 Wilson et al.
5,558,266 A 9/1996 Green et al.
5,562,241 A 10/1996 Knodel et al.
5,562,700 A 10/1996 Huitema et al.
5,562,701 A 10/1996 Huitema et al.
5,562,702 A 10/1996 Huitema et al.
5,564,615 A 10/1996 Bishop et al.
5,571,115 A 11/1996 Nicholas
5,571,285 A 11/1996 Chow et al.
5,579,978 A 12/1996 Green et al.
5,580,067 A 12/1996 Hamblin et al.
5,584,425 A 12/1996 Savage et al.
5,586,711 A 12/1996 Plyley et al.
5,588,581 A 12/1996 Conlon et al.
5,597,107 A 1/1997 Knodel et al.
5,601,224 A 2/1997 Bishop et al.
5,605,272 A 2/1997 Witt et al.
5,607,095 A 3/1997 Smith et al.
5,615,820 A 4/1997 Viola
5,626,587 A 5/1997 Bishop et al.
5,630,539 A 5/1997 Plyley et al.
5,634,584 A 6/1997 Okorocha et al.
5,636,779 A 6/1997 Palmer
5,657,921 A 8/1997 Young et al.
5,662,258 A 9/1997 Knodel et al.
5,662,662 A 9/1997 Bishop et al.
5,662,667 A 9/1997 Knodel
5,673,840 A 10/1997 Schulze et al.
5,673,841 A 10/1997 Schulze et al.
5,673,842 A 10/1997 Bittner et al.
5,676,674 A 10/1997 Bolanos et al.
5,678,748 A 10/1997 Plyley
5,680,982 A 10/1997 Schulze et al.
5,680,983 A 10/1997 Plyley et al.
5,697,542 A 12/1997 Knodel et al.
5,697,543 A 12/1997 Burdorff
5,704,534 A 1/1998 Huitema et al.
5,704,898 A 1/1998 Kokish
5,706,998 A 1/1998 Blyley et al.
5,709,334 A 1/1998 Sorrentino et al.
5,713,505 A 2/1998 Huitema
5,715,988 A 2/1998 Palmer
5,718,359 A 2/1998 Palmer et al.
5,732,871 A 3/1998 Clark et al.
5,735,445 A 4/1998 Vidal et al.
5,762,255 A 6/1998 Chrisman et al.
5,762,256 A 6/1998 Mastri et al.
5,779,130 A 7/1998 Alesi et al.
5,782,396 A 7/1998 Mastri et al.
5,782,397 A 7/1998 Koukline
5,785,232 A 7/1998 Vidal et al.
5,794,834 A 8/1998 Hamblin et al.

(56) References Cited

U.S. PATENT DOCUMENTS 5,797,536 A 8/1998 Smith et al.
5,797,537 A 8/1998 Oberlin et al.
5,797,538 A 8/1998 Heaton et al.
5,810,240 A 9/1998 Robertson
5,814,055 A 9/1998 Knodel et al.
5,820,009 A 10/1998 Melling et al.
5,829,662 A 11/1998 Allen et al.
5,860,995 A 1/1999 Berkelaar
5,865,361 A 2/1999 Milliman et al.
5,878,937 A 3/1999 Green et al.
5,878,938 A 3/1999 Bittner et al.
5,893,506 A 4/1999 Powell
5,894,979 A 4/1999 Powell
5,901,895 A 5/1999 Heaton et al.
5,918,791 A 7/1999 Sorrentino et al.
5,931,847 A 8/1999 Bittner et al.
5,954,259 A 9/1999 Viola et al.
5,964,394 A 10/1999 Robertson
D416,089 S 11/1999 Barton et al.
5,988,479 A 11/1999 Palmer
6,032,849 A 3/2000 Mastri et al.
6,053,390 A 4/2000 Green et al.
6,079,606 A 6/2000 Milliman et al.
6,109,500 A 8/2000 Alli et al.
6,131,789 A 10/2000 Schulze et al.
6,155,473 A 12/2000 Tompkins et al.
D441,865 S 5/2001 Racenet et al.
6,241,139 B1 6/2001 Milliman et al.
6,250,532 B1 6/2001 Green et al.
6,264,087 B1 7/2001 Whitman
6,270,453 B1 8/2001 Sakai
6,325,810 B1 12/2001 Hamilton et al.
6,330,965 B1 12/2001 Milliman et al.
6,488,196 B1 12/2002 Fenton, Jr.
6,550,757 B2 4/2003 Sesek
6,569,171 B2 5/2003 DeGuillebon et al.
6,595,509 B2 7/2003 Sesek
6,619,529 B2 9/2003 Green et al.
6,644,532 B2 11/2003 Green et al.
6,669,073 B2 12/2003 Milliman et al.
6,716,233 B1 4/2004 Whitman
6,786,382 B1 9/2004 Hoffman
6,817,508 B1 11/2004 Racenet et al.
6,821,282 B2 11/2004 Perry et al.
6,835,199 B2 12/2004 McGuckin, Jr. et al.
6,913,181 B2 7/2005 Mochizuki et al.
6,923,360 B2 8/2005 Sesek et al.
6,953,138 B1 10/2005 Dworak et al.
6,953,139 B2 10/2005 Milliman et al.
6,964,363 B2 11/2005 Wales et al.
6,978,921 B2 12/2005 Shelton, IV et al.
6,986,451 B1 1/2006 Mastri et al.
6,988,649 B2 1/2006 Shelton, IV et al.
7,000,818 B2 2/2006 Shelton, IV et al.
7,044,352 B2 5/2006 Shelton, IV et al.
7,044,353 B2 5/2006 Mastri et al.
7,044,947 B2 5/2006 de la Torre et al.
7,055,730 B2 6/2006 Ehrenfels et al.
7,070,083 B2 7/2006 Jankowski
7,097,089 B2 8/2006 Marczyk
7,097,650 B2 8/2006 Weller et al.
7,108,472 B2 9/2006 Norris et al.
7,128,253 B2 10/2006 Mastri et al.
7,140,527 B2 11/2006 Ehrenfels et al.
7,140,528 B2 11/2006 Shelton, IV
7,143,923 B2 12/2006 Shelton, IV et al.
7,143,924 B2 12/2006 Scirica et al.
7,147,139 B2 12/2006 Schwemberger et al.
7,213,736 B2 5/2007 Wales et al.
7,225,964 B2 6/2007 Mastri et al.
7,237,708 B1 7/2007 Guy et al.
7,258,262 B2 8/2007 Mastri et al.
7,275,674 B2 10/2007 Racenet et al.
7,278,562 B2 10/2007 Mastri et al.
7,290,692 B2 11/2007 Marks
7,293,685 B2 11/2007 Ehrenfels et al.
7,303,107 B2 12/2007 Milliman et al.
7,308,998 B2 12/2007 Mastri et al.
7,328,828 B2 2/2008 Ortiz et al.
7,334,717 B2 2/2008 Rethy et al.
7,380,695 B2 6/2008 Doll et al.
7,380,696 B2 6/2008 Shelton, IV et al.
7,398,908 B2 7/2008 Holsten et al.
7,399,310 B2 7/2008 Edoga et al.
7,401,721 B2 7/2008 Holsten et al.
7,404,508 B2 7/2008 Smith et al.
7,407,075 B2 8/2008 Holsten et al.
7,407,078 B2 8/2008 Shelton, IV et al.
7,416,101 B2 8/2008 Shelton, IV et al.
RE40,514 E 9/2008 Mastri et al.
7,419,080 B2 9/2008 Smith et al.
7,419,081 B2 9/2008 Ehrenfels et al.
7,422,136 B1 9/2008 Marczyk
7,422,139 B2 9/2008 Shelton, IV et al.
7,431,188 B1 10/2008 Marczyk
7,434,715 B2 10/2008 Shelton, IV et al.
7,434,716 B2 10/2008 Viola
7,455,208 B2 11/2008 Wales et al.
7,455,676 B2 11/2008 Holsten et al.
7,461,767 B2 12/2008 Viola et al.
7,464,846 B2 12/2008 Shelton, IV et al.
7,464,847 B2 12/2008 Viola et al.
7,464,849 B2 12/2008 Shelton, IV et al.
7,467,740 B2 12/2008 Shelton, IV et al.
7,472,814 B2 1/2009 Mastri et al.
7,472,815 B2 1/2009 Shelton, IV et al.
7,472,816 B2 1/2009 Holsten et al.
7,481,348 B2 1/2009 Marczyk
7,481,349 B2 1/2009 Holsten et al.
7,487,899 B2 2/2009 Shelton, IV et al.
7,490,749 B2 2/2009 Schall et al.
7,506,790 B2 3/2009 Shelton, IV
7,506,791 B2 3/2009 Omaits et al.
7,513,408 B2 4/2009 Shelton, IV et al.
7,530,484 B1 5/2009 Durrani
7,543,730 B1 6/2009 Marczyk
7,543,731 B2 6/2009 Green et al.
7,546,940 B2 6/2009 Milliman et al.
7,549,564 B2 6/2009 Boudreaux
7,552,854 B2 6/2009 Wixey et al.
7,556,186 B2 7/2009 Milliman
7,565,993 B2 7/2009 Milliman et al.
7,568,604 B2 8/2009 Ehrenfels et al.
7,588,174 B2 9/2009 Holsten et al.
7,588,175 B2 9/2009 Timm et al.
7,588,177 B2 9/2009 Racenet
7,604,151 B2 10/2009 Hess et al.
7,611,038 B2 11/2009 Racenet et al.
7,617,961 B2 11/2009 Viola
7,624,902 B2 12/2009 Marczyk et al.
7,631,793 B2 12/2009 Rethy et al.
7,635,074 B2 12/2009 Olson et al.
7,637,409 B2 12/2009 Marczyk
7,637,410 B2 12/2009 Marczyk
7,641,091 B2 1/2010 Olson et al.
7,641,093 B2 1/2010 Doll et al.
7,641,095 B2 1/2010 Viola
7,644,848 B2 1/2010 Swayze et al.
7,648,055 B2 1/2010 Marczyk
7,651,017 B2 1/2010 Ortiz et al.
7,654,431 B2 2/2010 Hueil et al.
7,658,311 B2 2/2010 Boudreaux
7,665,647 B2 2/2010 Shelton, IV et al.
7,669,746 B2 3/2010 Shelton, IV
7,670,334 B2 3/2010 Hueil et al.
7,673,781 B2 3/2010 Swayze et al.
7,682,367 B2 3/2010 Shah et al.
7,690,547 B2 4/2010 Racenet et al.
7,703,653 B2 4/2010 Shah et al.
7,717,312 B2 5/2010 Beetel
7,721,931 B2 5/2010 Shelton, IV et al.
7,721,933 B2 5/2010 Ehrenfels et al.
7,721,935 B2 5/2010 Racenet et al.
7,721,936 B2 5/2010 Shelton, IV et al.

(56) References Cited

U.S. PATENT DOCUMENTS 7,726,538 B2 6/2010 Holsten et al.
7,726,539 B2 6/2010 Holsten et al.
7,731,073 B2 6/2010 Wixey et al.
7,735,703 B2 6/2010 Morgan et al.
7,753,245 B2 7/2010 Boudreaux et al.
7,753,246 B2 7/2010 Scirica
7,757,925 B2 7/2010 Viola et al.
7,766,210 B2 8/2010 Shelton, IV et al.
7,770,774 B2 8/2010 Mastri et al.
7,780,054 B2 8/2010 Wales
7,780,055 B2 8/2010 Scirica et al.
7,784,662 B2 8/2010 Wales et al.
7,784,663 B2 8/2010 Shelton, IV
7,793,812 B2 9/2010 Moore et al.
7,798,386 B2 9/2010 Schall et al.
7,810,693 B2 10/2010 Broehl et al.
7,815,090 B2 10/2010 Marczyk
7,815,091 B2 10/2010 Marczyk
7,819,298 B2 10/2010 Hall et al.
7,819,896 B2 10/2010 Racenet
7,823,760 B2 11/2010 Zemlok et al.
7,828,188 B2 11/2010 Jankowski
7,828,189 B2 11/2010 Holsten et al.
7,837,079 B2 11/2010 Holsten et al.
7,837,081 B2 11/2010 Holsten et al.
7,845,534 B2 12/2010 Viola et al.
7,845,535 B2 12/2010 Scircia
7,845,537 B2 12/2010 Shelton, IV et al.
7,857,184 B2 12/2010 Viola
7,857,185 B2 12/2010 Swayze et al.
7,857,187 B2 12/2010 Milliman
7,861,906 B2 1/2011 Doll et al.
7,866,525 B2 1/2011 Scirica
7,866,527 B2 1/2011 Hall et al.
7,891,534 B2 2/2011 Wenchell et al.
7,905,381 B2 3/2011 Baxter, III et al.
7,909,220 B2 3/2011 Viola
7,909,221 B2 3/2011 Viola et al.
7,913,891 B2 3/2011 Doll et al.
7,914,543 B2 3/2011 Roth et al.
7,918,230 B2 4/2011 Whitman et al.
7,918,376 B1 4/2011 Knodel et al.
7,918,377 B2 4/2011 Measamer et al.
7,922,063 B2 4/2011 Zemlok et al.
7,934,628 B2 5/2011 Wenchell et al.
7,934,629 B2 5/2011 Wixey et al.
7,934,630 B2 5/2011 Shelton, IV et al.
7,942,300 B2 5/2011 Rethy et al.
7,954,685 B2 6/2011 Viola
7,954,686 B2 6/2011 Baxter, III et al.
7,959,050 B2 6/2011 Smith et al.
7,963,433 B2 6/2011 Whitman et al.
7,992,758 B2 8/2011 Whitman et al.
8,002,795 B2 8/2011 Beetel
8,006,887 B2 8/2011 Marczyk
8,007,513 B2 8/2011 Nalagatla et al.
8,008,598 B2 8/2011 Whitman et al.
8,011,550 B2 9/2011 Aranyi et al.
8,011,553 B2 9/2011 Mastri et al.
8,012,170 B2 9/2011 Whitman et al.
8,016,178 B2 9/2011 Olson et al.
8,020,742 B2 9/2011 Marczyk
8,020,743 B2 9/2011 Shelton, IV
8,028,885 B2 10/2011 Smith et al.
8,033,438 B2 10/2011 Scirica
8,033,440 B2 10/2011 Wenchell et al.
8,033,441 B2 10/2011 Marczyk
8,033,442 B2 10/2011 Racenet et al.
8,034,077 B2 10/2011 Smith et al.
8,038,046 B2 10/2011 Smith et al.
8,052,024 B2 11/2011 Viola et al.
8,056,788 B2 11/2011 Mastri et al.
8,056,789 B1 11/2011 White et al.
8,061,576 B2 11/2011 Cappola
8,061,577 B2 11/2011 Racenet et al.
8,070,033 B2 12/2011 Milliman et al.
8,070,034 B1 12/2011 Knodel
8,070,035 B2 12/2011 Holsten et al.
8,070,036 B1 12/2011 Knodel
8,074,861 B2 12/2011 Ehrenfels et al.
8,083,118 B2 12/2011 Milliman et al.
8,087,563 B2 1/2012 Milliman et al.
8,091,753 B2 1/2012 Viola
8,091,754 B2 1/2012 Ehrenfels et al.
8,092,493 B2 1/2012 Marczyk
8,100,309 B2 1/2012 Marczyk
8,113,406 B2 2/2012 Holsten et al.
8,113,407 B2 2/2012 Holsten et al.
8,113,408 B2 2/2012 Wenchell et al.
8,113,410 B2 2/2012 Hall et al.
8,118,207 B2 2/2012 Racenet et al.
8,123,100 B2 2/2012 Holsten et al.
8,127,976 B2 3/2012 Scirica et al.
8,136,712 B2 3/2012 Zingman
8,152,041 B2 4/2012 Kostrzewski
8,157,145 B2 4/2012 Shelton, IV et al.
8,157,150 B2 4/2012 Viola et al.
8,157,152 B2 4/2012 Holsten et al.
8,181,839 B2 5/2012 Beetel
8,186,555 B2 5/2012 Shelton, IV et al.
8,186,556 B2 5/2012 Viola
8,186,560 B2 5/2012 Hess et al.
8,191,752 B2 6/2012 Scirica
8,196,795 B2 6/2012 Moore et al.
8,201,721 B2 6/2012 Zemlok et al.
8,205,619 B2 6/2012 Shah et al.
8,205,780 B2 6/2012 Sorrentino et al.
8,205,781 B2 6/2012 Baxter et al.
8,210,411 B2 7/2012 Yates et al.
8,210,416 B2 7/2012 Milliman et al.
8,220,688 B2 7/2012 Laurent et al.
8,225,979 B2 7/2012 Farascioni et al.
8,231,040 B2 7/2012 Zemlok et al.
8,231,041 B2 7/2012 Marczyk et al.
8,235,274 B2 8/2012 Cappola
8,236,010 B2 8/2012 Ortiz et al.
8,240,536 B2 8/2012 Marczyk
8,240,537 B2 8/2012 Marczyk
8,241,322 B2 8/2012 Whitman et al.
8,245,898 B2 8/2012 Smith et al.
8,245,899 B2 8/2012 Swensgard et al.
8,245,900 B2 8/2012 Scirica
8,256,656 B2 9/2012 Milliman et al.
8,272,552 B2 9/2012 Holsten et al.
8,272,554 B2 9/2012 Whitman et al.
8,281,972 B2 10/2012 Wixey et al.
8,281,973 B2 10/2012 Wenchell et al.
8,286,846 B2 10/2012 Smith et al.
8,292,146 B2 10/2012 Holsten et al.
8,292,148 B2 10/2012 Viola
8,292,151 B2 10/2012 Viola
8,292,152 B2 10/2012 Milliman et al.
8,292,153 B2 10/2012 Jankowski
8,292,157 B2 10/2012 Smith et al.
8,308,041 B2 11/2012 Kostrzewski
8,308,043 B2 11/2012 Bindra et al.
8,317,070 B2 11/2012 Hueil et al.
8,322,455 B2 12/2012 Shelton, IV et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,348,125 B2 1/2013 Viola et al.
8,348,129 B2 1/2013 Bedi et al.
8,348,131 B2 1/2013 Omaits et al.
8,353,440 B2 1/2013 Whitman et al.
8,360,297 B2 1/2013 Shelton, IV et al.
8,360,299 B2 1/2013 Zemlok et al.
8,371,491 B2 * 2/2013 Huitema .......... A61B 17/07292 227/176.1
8,393,513 B2 3/2013 Jankowski
8,397,972 B2 3/2013 Kostrzewski
8,397,973 B1 3/2013 Hausen

(56) References Cited

U.S. PATENT DOCUMENTS 8,403,198 B2 3/2013 Sorrentino et al.
8,413,868 B2 4/2013 Cappola
8,414,577 B2 4/2013 Boudreaux et al.
8,418,906 B2 4/2013 Farascioni et al.
8,418,907 B2 4/2013 Johnson et al.
8,418,908 B1 4/2013 Beardsley
8,419,768 B2 4/2013 Marczyk
8,439,246 B1 5/2013 Knodel
8,444,036 B2 5/2013 Shelton, IV
8,453,907 B2 6/2013 Laurent et al.
8,453,912 B2 6/2013 Mastri et al.
8,453,913 B2 6/2013 Milliman
8,459,520 B2 6/2013 Giordano et al.
8,459,522 B2 6/2013 Marczyk
8,464,922 B2 6/2013 Marczyk
8,469,252 B2 6/2013 Holcomb et al.
8,479,967 B2 7/2013 Marczyk
8,496,152 B2 7/2013 Viola
8,496,155 B2 7/2013 Knodel
8,496,156 B2 7/2013 Sniffin et al.
8,496,683 B2 7/2013 Prommersberger et al.
8,505,799 B2 8/2013 Viola et al.
8,505,801 B2 8/2013 Ehrenfels et al.
8,517,239 B2 8/2013 Scheib et al.
8,517,240 B1 8/2013 Mata et al.
8,523,043 B2 9/2013 Ullrich et al.
8,540,130 B2 9/2013 Moore et al.
8,540,133 B2 9/2013 Bedi et al.
8,540,625 B2 9/2013 Miyoshi
8,544,712 B2 10/2013 Jankowski
8,556,151 B2 10/2013 Viola
8,556,152 B2 10/2013 Marczyk et al.
8,556,153 B1 10/2013 Knodel
8,561,871 B2 10/2013 Rajappa et al.
8,561,874 B2 10/2013 Scirica
8,573,459 B2 11/2013 Smith et al.
8,573,460 B2 11/2013 Cappola
8,573,462 B2 11/2013 Smith et al.
8,573,463 B2 11/2013 Scirica et al.
8,573,464 B2 11/2013 Nalagatla et al.
8,579,176 B2 11/2013 Smith et al.
8,579,177 B2 11/2013 Beetel
8,584,919 B2 11/2013 Hueil et al.
8,584,921 B2 11/2013 Scirica
8,596,513 B2 12/2013 Olson
8,608,043 B2 12/2013 Scirica
8,608,045 B2 12/2013 Smith et al.
8,616,427 B2 12/2013 Viola
8,622,274 B2 1/2014 Yates et al.
8,627,992 B2 1/2014 Edoga et al.
8,627,993 B2 1/2014 Smith et al.
8,627,995 B2 1/2014 Smith et al.
8,631,990 B1 1/2014 Park et al.
8,632,525 B2 1/2014 Kerr et al.
8,632,535 B2 1/2014 Shelton, IV et al.
8,636,189 B1 1/2014 Knodel et al.
8,636,190 B2 1/2014 Zemlok et al.
8,636,192 B2 1/2014 Farascioni et al.
8,636,193 B2 1/2014 Whitman et al.
8,636,762 B2 1/2014 Whitman et al.
8,636,766 B2 1/2014 Milliman et al.
8,657,174 B2 2/2014 Yates et al.
8,657,176 B2 2/2014 Shelton, IV et al.
8,657,178 B2 2/2014 Hueil et al.
8,672,209 B2 3/2014 Crainich
8,672,951 B2 3/2014 Smith et al.
8,685,004 B2 4/2014 Zemlock et al.
8,695,865 B2 4/2014 Smith et al.
8,696,665 B2 4/2014 Hunt et al.
8,708,211 B2 4/2014 Zemlok et al.
8,708,213 B2 4/2014 Shelton, IV et al.
8,714,352 B2 * 5/2014 Farascioni .......... A61B 17/068
206/363
8,740,034 B2 6/2014 Morgan et al.
8,740,035 B2 6/2014 Mastri et al.
8,740,036 B2 6/2014 Williams
8,752,748 B2 6/2014 Whitman et al.
8,763,876 B2 7/2014 Kostrzewski
8,770,458 B2 7/2014 Scirica
8,770,459 B2 7/2014 Racenet et al.
8,789,741 B2 7/2014 Baxter, III et al.
8,800,839 B2 8/2014 Beetel
8,800,840 B2 8/2014 Jankowski
8,800,841 B2 8/2014 Ellerhorst et al.
8,806,973 B2 8/2014 Ross et al.
8,807,414 B2 8/2014 Ross et al.
8,820,603 B2 9/2014 Shelton, IV et al.
8,820,608 B2 9/2014 Miyamoto
8,833,631 B2 9/2014 Munro, III et al.
8,840,003 B2 9/2014 Morgan et al.
8,858,571 B2 10/2014 Shelton, IV et al.
8,875,971 B2 11/2014 Hall et al.
8,875,972 B2 11/2014 Weisenburgh, II et al.
8,887,979 B2 11/2014 Mastri et al.
8,899,462 B2 12/2014 Kostrzewski et al.
8,899,463 B2 12/2014 Schall et al.
8,905,288 B2 12/2014 Wenchell
8,920,435 B2 12/2014 Smith et al.
8,925,783 B2 1/2015 Zemlok et al.
8,931,679 B2 1/2015 Kostrzewski
8,931,683 B2 1/2015 Racenet et al.
8,939,343 B2 1/2015 Milliman et al.
8,967,444 B2 3/2015 Beetel
8,967,445 B2 * 3/2015 Kostrzewski ........ A61B 17/068
227/176.1
8,967,446 B2 3/2015 Beardsley et al.
8,967,447 B2 3/2015 Hartoumbekis
8,968,276 B2 3/2015 Zemlok et al.
8,973,803 B2 3/2015 Hall et al.
8,979,827 B2 3/2015 Cappola
9,004,340 B2 4/2015 Scirica
9,010,611 B2 4/2015 Ross et al.
9,016,541 B2 4/2015 Viola et al.
9,016,545 B2 4/2015 Aranyi et al.
9,022,271 B2 5/2015 Scirica
9,023,014 B2 5/2015 Chowaniec et al.
9,027,817 B2 5/2015 Milliman et al.
9,027,818 B2 5/2015 Scirica et al.
9,033,202 B2 5/2015 Scirica
9,038,880 B1 5/2015 Donohoe
9,055,943 B2 6/2015 Zemlok et al.
9,072,515 B2 7/2015 Hall et al.
9,084,601 B2 7/2015 Moore et al.
9,101,358 B2 8/2015 Kerr et al.
9,161,813 B2 10/2015 Benamou
9,204,876 B2 12/2015 Cappola et al.
9,237,890 B2 1/2016 Kostrzewski
9,265,585 B2 2/2016 Wingardner et al.
9,282,966 B2 3/2016 Shelton, IV et al.
9,386,984 B2 7/2016 Aronhalt et al.
9,402,629 B2 8/2016 Ehrenfels et al.
9,510,830 B2 12/2016 Shelton, IV et al.
9,532,782 B2 1/2017 Kostrzewski
9,662,108 B2 5/2017 Williams
9,706,993 B2 * 7/2017 Hessler ............. A61B 17/0682
9,737,302 B2 8/2017 Shelton, IV et al.
9,737,303 B2 8/2017 Shelton, IV et al.
9,797,486 B2 10/2017 Zergiebel et al.
10,499,918 B2 * 12/2019 Schellin .......... A61B 17/07292
2002/0025243 A1 2/2002 Heck
2002/0029044 A1 3/2002 Monassevitch et al.
2002/0062136 A1 5/2002 Hillstead
2002/0120279 A1 8/2002 Deguillebon et al.
2003/0130677 A1 7/2003 Whitman et al.
2004/0006372 A1 1/2004 Racenet et al.
2004/0138705 A1 7/2004 Heino et al.
2005/0234478 A1 10/2005 Wixey
2006/0097026 A1 5/2006 Shelton, IV
2006/0100644 A1 5/2006 Viola
2006/0180634 A1 8/2006 Shelton, IV et al.
2006/0235442 A1 10/2006 Huitema
2006/0289602 A1 12/2006 Wales et al.
2007/0034664 A1 2/2007 Jiang
2007/0039997 A1 2/2007 Mather et al.

(56) References Cited

U.S. PATENT DOCUMENTS

2007/0057014 A1 3/2007 Whitman et al.
2007/0068990 A1 3/2007 Shelton, IV et al.
2007/0084897 A1 4/2007 Shelton, IV et al.
2007/0102472 A1 5/2007 Shelton, IV
2007/0119901 A1 5/2007 Ehrenfels et al.
2007/0131732 A1 6/2007 Holsten et al.
2007/0175950 A1 8/2007 Shelton, IV et al.
2007/0175951 A1 8/2007 Shelton, IV et al.
2008/0029574 A1 2/2008 Shelton et al.
2008/0029575 A1 2/2008 Shelton et al.
2008/0041918 A1 2/2008 Holsten et al.
2008/0078807 A1 4/2008 Hess et al.
2008/0083807 A1 4/2008 Beardsley et al.
2008/0169333 A1 7/2008 Shelton et al.
2008/0179375 A1 7/2008 Scirica
2008/0255607 A1 10/2008 Zemlok
2009/0001129 A1 1/2009 Marczyk
2009/0001130 A1 1/2009 Hess et al.
2009/0026245 A1 1/2009 Holsten et al.
2009/0048589 A1 2/2009 Takashino et al.
2009/0057369 A1 3/2009 Smith et al.
2009/0090763 A1 4/2009 Zemlok et al.
2009/0143806 A1 6/2009 Witt et al.
2009/0198272 A1 8/2009 Kerver et al.
2009/0206131 A1 8/2009 Weisenburgh, II et al.
2009/0206133 A1 8/2009 Morgan et al.
2009/0206137 A1 8/2009 Hall et al.
2009/0277948 A1 11/2009 Beardsley et al.
2009/0277949 A1 11/2009 Viola et al.
2010/0069942 A1 3/2010 Shelton, IV
2010/0072258 A1 3/2010 Farascioni et al.
2010/0089970 A1 4/2010 Smith et al.
2010/0193566 A1 8/2010 Scheib et al.
2010/0230465 A1 9/2010 Smith et al.
2010/0331820 A1 12/2010 Prisco et al.
2011/0036892 A1 2/2011 Marczyk et al.
2011/0042440 A1 2/2011 Holsten et al.
2011/0087276 A1 4/2011 Bedi et al.
2011/0108601 A1 5/2011 Clark et al.
2011/0108603 A1 5/2011 Racenet et al.
2011/0121049 A1 5/2011 Malinouskas et al.
2011/0125138 A1 5/2011 Malinouskas et al.
2011/0127185 A1 6/2011 Ward
2011/0139852 A1 6/2011 Zingman
2011/0147433 A1 6/2011 Shelton, IV et al.
2011/0155784 A1 6/2011 Shelton, IV et al.
2011/0155787 A1 6/2011 Laurent et al.
2011/0290851 A1 12/2011 Shelton, IV et al.
2011/0290853 A1 12/2011 Shelton, IV et al.
2012/0061446 A1 3/2012 Knodel et al.
2012/0074198 A1 3/2012 Huitema et al.
2012/0074200 A1 3/2012 Schmid et al.
2012/0078243 A1 3/2012 Worrell et al.
2012/0080482 A1 4/2012 Schall et al.
2012/0080498 A1 4/2012 Shelton, IV et al.
2012/0091182 A1 4/2012 Marczyk
2012/0109186 A1 5/2012 Parrott et al.
2012/0168487 A1 7/2012 Holsten et al.
2012/0193396 A1 8/2012 Zemlok et al.
2012/0203247 A1 8/2012 Shelton, IV et al.
2012/0211542 A1 8/2012 Racenet
2012/0239009 A1 9/2012 Mollere et al.
2012/0253298 A1 10/2012 Henderson et al.
2012/0286022 A1 11/2012 Olson et al.
2012/0318844 A1 12/2012 Shelton, IV et al.
2012/0325893 A1 12/2012 Pastorelli et al.
2013/0001270 A1 1/2013 Kostrzewski
2013/0012958 A1 1/2013 Marczyk et al.
2013/0015229 A1 1/2013 Viola
2013/0015230 A1 1/2013 Wixey et al.
2013/0015232 A1 1/2013 Smith et al.
2013/0015233 A1 1/2013 Viola
2013/0020375 A1 1/2013 Shelton, IV et al.
2013/0037595 A1 2/2013 Gupta et al.
2013/0048697 A1 2/2013 Shelton, IV et al.
2013/0056521 A1 3/2013 Swensgard
2013/0079814 A1 3/2013 Hess et al.
2013/0087603 A1 4/2013 Viola
2013/0092717 A1 4/2013 Marczyk et al.
2013/0098964 A1 4/2013 Smith et al.
2013/0098965 A1 4/2013 Kostrzewski et al.
2013/0098969 A1 4/2013 Scirica et al.
2013/0105545 A1 5/2013 Burbank
2013/0105547 A1 5/2013 Beardsley
2013/0105548 A1 5/2013 Hodgkinson et al.
2013/0105549 A1 5/2013 Holsten et al.
2013/0112730 A1 5/2013 Whitman et al.
2013/0112731 A1 5/2013 Hodgkinson
2013/0126583 A1 5/2013 Hueil et al.
2013/0126586 A1 5/2013 Zhang et al.
2013/0146640 A1 6/2013 Jankowski
2013/0172928 A1 7/2013 Kostrzewski
2013/0172929 A1 7/2013 Hess et al.
2013/0175317 A1 7/2013 Yates et al.
2013/0175322 A1 7/2013 Yates et al.
2013/0184718 A1 7/2013 Smith et al.
2013/0186931 A1 7/2013 Beardsley
2013/0186932 A1 7/2013 Shelton, IV et al.
2013/0186933 A1 7/2013 Shelton, IV et al.
2013/0193188 A1 8/2013 Shelton, IV et al.
2013/0200132 A1 8/2013 Moore et al.
2013/0206816 A1 8/2013 Penna
2013/0214025 A1 8/2013 Zemlok et al.
2013/0221065 A1 8/2013 Aronhalt et al.
2013/0240604 A1 9/2013 Knodel
2013/0248582 A1 9/2013 Scirica
2013/0256370 A1 10/2013 Smith et al.
2013/0256371 A1 10/2013 Shelton, IV
2013/0270321 A1 10/2013 Marczyk
2013/0270323 A1 10/2013 Marczyk
2013/0284789 A1 10/2013 Smith et al.
2013/0284791 A1 10/2013 Olson et al.
2013/0299552 A1 11/2013 Viola
2013/0306702 A1 11/2013 Viola et al.
2013/0306703 A1 11/2013 Ehrenfels et al.
2013/0306706 A1 11/2013 Knodel
2013/0313303 A1 11/2013 Shelton, IV et al.
2013/0327809 A1 12/2013 Shelton, IV et al.
2013/0327810 A1 12/2013 Swayze et al.
2013/0334278 A1 12/2013 Kerr et al.
2013/0334280 A1 12/2013 Krehel et al.
2013/0334281 A1 12/2013 Williams
2013/0334283 A1 12/2013 Swayze et al.
2013/0334284 A1 12/2013 Swayze et al.
2013/0334285 A1 12/2013 Swayze et al.
2013/0334286 A1 12/2013 Swayze et al.
2013/0334287 A1 12/2013 Shelton, IV
2013/0334288 A1 12/2013 Shelton, IV
2014/0008412 A1* 1/2014 Zemlok .................. A61B 90/90 227/176.1
2014/0014704 A1 1/2014 Onukuri et al.
2014/0014707 A1 1/2014 Onukuri et al.
2014/0021239 A1 1/2014 Kostrzewski
2014/0025046 A1 1/2014 Williams et al.
2014/0027491 A1 1/2014 Beardsley et al.
2014/0027493 A1 1/2014 Jankowski
2014/0042204 A1 2/2014 Beetel
2014/0103092 A1 4/2014 Kostrzewski et al.
2014/0103093 A1 4/2014 Koch, Jr. et al.
2014/0107640 A1 4/2014 Yates et al.
2014/0110453 A1 4/2014 Wingardner et al.
2014/0131416 A1 5/2014 Whitman et al.
2014/0135832 A1 5/2014 Park et al.
2014/0151433 A1 6/2014 Shelton, IV et al.
2014/0151434 A1 6/2014 Shelton, IV et al.
2014/0158746 A1 6/2014 Mastri et al.
2014/0166727 A1 6/2014 Swayze et al.
2014/0175146 A1 6/2014 Knodel
2014/0175149 A1 6/2014 Smith et al.
2014/0203063 A1 7/2014 Hessler et al.
2014/0205637 A1 7/2014 Widenhouse et al.
2014/0224856 A1 8/2014 Smith et al.
2014/0236173 A1 8/2014 Scirica et al.
2014/0236184 A1 8/2014 Leimbach

(56) References Cited

U.S. PATENT DOCUMENTS

2014/0239038 A1 8/2014 Leimbach et al.
2014/0239041 A1 8/2014 Zerkle et al.
2014/0239044 A1 8/2014 Hoffman
2014/0246474 A1 9/2014 Hall et al.
2014/0246475 A1 9/2014 Hall et al.
2014/0246478 A1 9/2014 Baber et al.
2014/0246479 A1 9/2014 Baber et al.
2014/0252065 A1* 9/2014 Hessler .............. A61B 17/0682 227/176.1
2014/0260746 A1 9/2014 Sakaguchi et al.
2014/0263537 A1 9/2014 Leimbach et al.
2014/0263539 A1 9/2014 Leimbach et al.
2014/0263541 A1 9/2014 Leimbach et al.
2014/0263542 A1 9/2014 Leimbach et al.
2014/0263543 A1 9/2014 Leimbach et al.
2014/0263545 A1 9/2014 Williams et al.
2014/0263546 A1 9/2014 Aranyi
2014/0263550 A1 9/2014 Aranyi et al.
2014/0263553 A1 9/2014 Leimbach et al.
2014/0263554 A1 9/2014 Leimbach et al.
2014/0263555 A1 9/2014 Hufnagel et al.
2014/0263559 A1 9/2014 Williams et al.
2014/0263562 A1 9/2014 Patel et al.
2014/0263564 A1 9/2014 Leimbach et al.
2014/0263565 A1 9/2014 Lytle, IV et al.
2014/0263566 A1 9/2014 Williams et al.
2014/0263567 A1 9/2014 Williams et al.
2014/0263568 A1 9/2014 Williams et al.
2014/0263569 A1 9/2014 Williams et al.
2014/0263570 A1 9/2014 Hopkins et al.
2014/0263571 A1 9/2014 Morgan et al.
2014/0263572 A1 9/2014 Shelton, IV et al.
2014/0284372 A1 9/2014 Kostrzewski
2014/0291378 A1 10/2014 Shelton, IV et al.
2014/0299649 A1 10/2014 Shelton, IV et al.
2014/0305986 A1 10/2014 Hall et al.
2014/0305988 A1 10/2014 Boudreaux et al.
2014/0305992 A1 10/2014 Kimsey et al.
2014/0305994 A1 10/2014 Parihar et al.
2014/0353359 A1 12/2014 Hall et al.
2015/0008248 A1 1/2015 Giordano et al.
2015/0034697 A1 2/2015 Mastri et al.
2015/0041518 A1 2/2015 Shelton, IV et al.
2015/0053738 A1 2/2015 Morgan et al.
2015/0053740 A1 2/2015 Shelton, IV
2015/0053741 A1 2/2015 Shelton, IV et al.
2015/0053742 A1 2/2015 Shelton, IV et al.
2015/0053743 A1 2/2015 Yates et al.
2015/0053744 A1 2/2015 Swayze et al.
2015/0053745 A1 2/2015 Yates et al.
2015/0053746 A1 2/2015 Shelton, IV et al.
2015/0053748 A1 2/2015 Yates et al.
2015/0053749 A1 2/2015 Shelton, IV et al.
2015/0054753 A1 2/2015 Morgan et al.
2015/0060516 A1 3/2015 Collings et al.
2015/0060517 A1 3/2015 Williams
2015/0060521 A1 3/2015 Weisenburgh, II et al.
2015/0076205 A1 3/2015 Zergiebel
2015/0076206 A1 3/2015 Sapre
2015/0076209 A1 3/2015 Shelton, IV et al.
2015/0076210 A1 3/2015 Shelton, IV et al.
2015/0076212 A1 3/2015 Shelton, IV
2015/0083781 A1 3/2015 Giordano et al.
2015/0083783 A1 3/2015 Shelton, IV et al.
2015/0090760 A1 4/2015 Giordano et al.
2015/0090761 A1 4/2015 Giordano et al.
2015/0090762 A1 4/2015 Giordano et al.
2015/0090764 A1 4/2015 Zemlok et al.
2015/0108201 A1 4/2015 Williams
2015/0122872 A1 5/2015 Olson et al.
2015/0127046 A1 5/2015 Peterson
2015/0129631 A1 5/2015 Beetel
2015/0129634 A1 5/2015 Shelton, IV et al.
2015/0133995 A1 5/2015 Shelton, IV et al.
2015/0133996 A1 5/2015 Shelton, IV et al.
2015/0134076 A1 5/2015 Shelton, IV et al.
2015/0144678 A1 5/2015 Hall et al.
2015/0201935 A1 7/2015 Weisenburgh, II et al.
2015/0208902 A1 7/2015 Okamoto
2015/0245834 A1 9/2015 Scirica et al.
2015/0272576 A1 10/2015 Cappola
2015/0289873 A1 10/2015 Shelton, IV et al.
2015/0297221 A1 10/2015 Kerr et al.
2015/0297222 A1* 10/2015 Huitema .............. A61B 17/068 227/176.1
2015/0297233 A1 10/2015 Huitema et al.
2015/0351765 A1* 12/2015 Valentine ............ G06F 11/1464 227/176.1
2015/0380187 A1 12/2015 Zergiebel et al.
2016/0000439 A1 1/2016 Weisenburgh, II et al.
2016/0000440 A1 1/2016 Weisenburgh, II et al.
2016/0058447 A1 3/2016 Posada et al.
2016/0058492 A1 3/2016 Yates et al.
2016/0128694 A1* 5/2016 Baxter, III ........... A61B 17/105 227/176.1
2016/0183948 A1 6/2016 Shelton, IV et al.
2016/0310204 A1 10/2016 McHenry et al.
2016/0338702 A1 11/2016 Ehrenfels et al.
2016/0374672 A1 12/2016 Bear et al.
2016/0374675 A1 12/2016 Shelton, IV et al.
2017/0007241 A1 1/2017 Shelton, IV et al.
2017/0007242 A1 1/2017 Shelton, IV et al.
2017/0007243 A1 1/2017 Shelton, IV et al.
2017/0007249 A1 1/2017 Shelton, IV et al.
2017/0231633 A1 8/2017 Marczyk et al.
2017/0245856 A1 8/2017 Baxter, III et al.
2017/0245858 A1 8/2017 Williams
2017/0281161 A1 10/2017 Shelton, IV et al.
2017/0281165 A1 10/2017 Harris et al.
2017/0281168 A1 10/2017 Shelton, IV et al.
2017/0290583 A1 10/2017 Reed et al.
2017/0290584 A1 10/2017 Jasemian et al.
2018/0168643 A1* 6/2018 Shelton, IV ........... A61B 34/30
2019/0261984 A1 8/2019 Nelson et al.
2020/0268381 A1 8/2020 Roberts et al.

FOREIGN PATENT DOCUMENTS

EP 0 514 139 A2 11/1992
EP 0 536 903 A2 4/1993
EP 0 596 543 A1 5/1994
EP 1 523 944 A1 4/2005
EP 1 759 812 A1 3/2007
EP 1 915 953 A1 4/2008
EP 1 479 348 B1 7/2008
EP 2 044 893 A2 9/2008
EP 2 005 902 A2 12/2008
EP 2 090 241 A1 8/2009
EP 2 263 568 A2 12/2010
EP 2 361 562 A1 8/2011
EP 2 462 875 A2 6/2012
EP 2 486 859 A2 8/2012
EP 2 764 833 A2 8/2014
EP 2 772 192 A1 9/2014
EP 2 777 530 A1 9/2014
EP 2 815 705 A1 12/2014
EP 2 923 661 A2 3/2015
EP 2 853 204 A1 4/2015
EP 2 891 462 A1 7/2015
EP 2 926 742 A1 10/2015
EP 2 942 020 A2 11/2015
EP 2 959 841 A1 12/2015
EP 3 135 225 A2 3/2017
EP 3 238 639 A2 3/2017
EP 3 338 653 A1 6/2018
EP 3 338 698 A1 6/2018
EP 3 338 702 A1 6/2018
JP 2001-087272 A 4/2001
RU 2063710 7/1996
WO WO 83/02247 A1 7/1983
WO WO 94/24947 A1 11/1994
WO WO 02/30296 A2 4/2002
WO WO 02/096327 A2 12/2002
WO WO 2003/094747 A1 11/2003

(56) References Cited

FOREIGN PATENT DOCUMENTS

| | | | |
|---|---|---|---|
| WO | WO 2004/032762 | A1 | 4/2004 |
| WO | WO 2012/052729 | A1 | 4/2012 |
| WO | WO 2014/139440 | A1 | 9/2014 |
| WO | WO 2020/077531 | A1 | 4/2020 |

OTHER PUBLICATIONS

International Searching Authority, U.S., The International Search Report and the Written Opinion of the International Searching authority for international application PCT/US2014/027768, titled "Surgical Stapler with Expandable Jaw", mailed Jul. 25, 2014, 17 pgs.

The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.

International Searching Authority, U.S., The International Search Report and the Written Opinion of the International Searching authority for international application PCT/US2015/0035379, titled "Surgical Stapler with Circumferential Firing", mailed Sep. 15, 2015, 22 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentabilityfor International Application No. PCT/US2015/035379, entitled "Surgical Stapler with Circumferential Firing," dated Dec. 22, 2016, 14 pgs.

The International Bureau of WIPO, International Preliminary Report on Patentabilityfor International Application No. PCT/US2015/050103, titled "Surgical Stapler With Self-Adjusting Staple Height," dated Mar. 30, 2017, 12 pgs.

European Patent Office, European Search Report for European Application No. EP 14764812.5, entitled "Surgical Stapler Having Actuation Mechanism with Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

European Patent Office, The International Search Report and the Written Opinion of the International Searching Authority for International Application No. PCT/US2017/027269, entitled "Reload Shaft Assembly for Surgical Stapler," mailed Sep. 12, 2017, 22 pgs.

European Patent Office, The International Search Report and the Written Opinion of the International Searching Authority for International Application No. PCT/US2017/027213, entitled "Surgical Stapler Having a Powered Handle," mailed Sep. 13, 2017, 17 pgs.

European Patent Office, The International Search Report and the Written Opinion of the International Searching Authority for International Application No. PCT/US2017/027142, entitled "Surgical Stapler Having Articulation Mechanism," mailed Sep. 14, 2017, 21 pgs.

European Patent Office, The International Search Report and Written Opinion of the International Searching Authority for International Application No. PCT/US2016/045993 titled "Surgical Stapler Having Locking Articulation Joint", mailed Jan. 24, 2017, 20 pgs.

European Patent Office, Partial European Search Report for European Application No. EP 14762896.0, entitled "Surgical Stapler with Expandable Jaw," dated Apr. 10, 2017, 6 pgs.

The International Bureau of Wipo, International Preliminary Report on Patentability, for International Application No. PCT/US2016/045993, entitled "Surgical Stapler Having Locking Articulation Joint," dated Feb. 15, 2018, 13 pgs.

European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.

The International Bureau of WIPO, International Preliminary Report on Patentability, for International Application No. PCT/US2017/027213, entitled "Surgical Stapler Having Powered Handle," dated Oct. 25, 2018, 9 pgs.

The International Bureau of WIPO, International Preliminary Report on Patentability, for International Application No. PCT/US2017/027269, entitled "Reload Shaft Assembly for Surgical Stapler," dated Oct. 25, 2018, 12 pgs.

European Patent Office, Extended European Search Report for European Application No. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," mailed Jul. 19, 2019, 24 pgs.

European Patent Office, Extended European Search Report for European Application No. EP 19150575.9, entitled "Surgical Stapler Having Actuation Mechanism with Rotatable Shaft," dated Aug. 21, 2019, 5 pgs.

European Patent Office, Extended European Search Report for European Application No. EP 19180055.6, entitled "Surgical Stapler with Circumferential Firing," dated Sep. 20, 2019, 8 pgs.

European Patent Office, The International Search Report and the Written Opinion of the International Searching Authority for International Application No. PCT/US2020/019938, entitled "Surgical Stapling Instrument Having a Two-Position Mechanism," mailed Jun. 18, 2020, 16 pgs.

European Patent Office, Extended European Search Report for European Application No. EP 20157713.7, entitled "Surgical Stapler with Expandable Jaw," dated May 11, 2020, 6 pgs.

International Searching Authority/ EPO, Invitation to Pay Additional Fees forPCTUS2020/025496, entitled "Reload Cover for Surgical Stapling System," dated Jun. 18, 2019, 15 pgs.

European Patent Office, Extended European Search Report for European Application No. EP 20161294.2, entitled "Surgical Stapler with Self-Adjusting Staple Height," dated Jun. 22, 2020, 6 pgs.

European Patent Office, The International Search Report and the Written Opinion of the International Searching Authority for International Application No. PCT/US2020/025496, entitled "Reload Cover for Surgical Stapling System," mailed Aug. 13, 2020, 20 pgs.

The International Bureau of WIPO, International Preliminary Report on Patentability, for International Application No. PCT/US2019/019867, entitled "Surgical Stapler Having a Powered Handle," dated Sep. 3, 2020, 16 pgs.

European Patent Office, Extended European Search Report for European Application No. EP 20197859.0, entitled "Surgical Stapler with Circumferential Firing," dated Jan. 28, 2021, 13 pgs.

European Patent Office, The International Search Report and Written Opinion for International Application No. PCT/US2020/067540, mailed May 3, 2021, entitled "Electrosurgical System with Tissue and Maximum Current Identification," 12 pages.

(56) References Cited

OTHER PUBLICATIONS

European Patent Office, Extended European Search Report for European Application No. EP 21162419.2, entitled "Surgical Stapler Having Articulation Mechanism," dated Jun. 22, 2021, 10 pgs.
The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.
European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" mailed Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" mailed Feb. 11, 2022, 15 pgs.
European Patent Office, The International Search Report and the Written Opinion of the International Searching Authority for International Application No. PCT/US2021/057365, entitled "Surgical Stapler Having a Powered Handle" mailed Apr. 13, 2022, 21 pgs.
European Patent Office, The International Search Report and the Written Opinion of the International Searching Authority for International Application No. PCT/US2022/012452, entitled "Surgical Stapler Having Shaft Recognition Mechanism" mailed Apr. 13, 2022, 13 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203464.7, entitled "Surgical Stapler with Partial Pockets," dated Dec. 20, 2022, 9 pgs.
European Patent Office, Extended European Search Report for European Application No. EP 22203599.0, entitled "Surgical Stapler Having a Powered Handle," dated Feb. 7, 2023, 7 pgs.
The International Bureau of WIPO, International Preliminary Report on Patentability, for International Application No. PCT/US2021/057231, entitled "Material Combinations and Processing Methods for a Surgical Instrument," dated May 11, 2023, 10 pgs.
The International Bureau of WIPO, International Preliminary Report on Patentability, for International Application No. PCT/US2021/057278, entitled "Actuation Shaft Retention Mechanism for Surgical Stapler," dated May 11, 2023, 10 pgs.
The International Bureau of WIPO, International Preliminary Report on Patentability, for International Application No. PCT/US2021/057365, entitled "Surgical Stapler Having a Powered Handle," dated May 11, 2023, 14 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.
European Patent Office, Extended European Search Report for European Application No. EP 23185918.2, entitled "Surgical Stapler Having Actuation Mechanism with Rotatable Shaft," dated Sep. 22, 2023, 5 pgs.
European Patent Office, Extended European Search Report for European Application No. EP 23198045.9, entitled "Reload Shaft Assembly for Surgical Stapler," dated Oct. 25, 2023, 12 pgs.
European Patent Office, Partial Extended European Search Report for European Patent Application No. 23198488.1, titled "Surgical Stapler with Self-Adjusting Staple Height," dated Jan. 23, 2024, 8 pgs.

* cited by examiner

22

30
20
32
24
132
34

150
162

152
152
164
164

170
150
164
164

RELOAD COVER FOR SURGICAL STAPLING SYSTEM

CROSS-REFERENCE TO RELATED APPLICATIONS

This application is a continuation of U.S. patent application Ser. No. 18/338,644 entitled "Reload Cover for Surgical Stapling System" filed on Jun. 21, 2023 which is a continuation of U.S. patent application Ser. No. 16/833,288 entitled "Reload Cover for Surgical Stapling System" filed on Mar. 27, 2020, now issued U.S. Pat. No. 11,717,293, which claims priority to and benefit of U.S. Provisional Patent Application Ser. No. 62/826,194 entitled "Reload Cover for Surgical Stapling System" filed on Mar. 29, 2019, each of which is incorporated herein by reference in its entirety.

BACKGROUND OF THE INVENTION

Field of the Invention

The present application relates generally to surgical occlusion instruments and, more particularly, to surgical staplers having reloads with removable covers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

Surgical staplers can further include replaceable reload cartridges such that multiple cartridges can be used with a stapler in a single surgical procedure. Further improvements to the reload cartridges are desirable to facilitate proper placement of the initial and each subsequent reload cartridges for use in the surgical stapler.

SUMMARY OF THE INVENTION

In certain embodiments, a surgical stapling device is provided herein. The surgical stapling device comprises an elongate shaft, a jaw assembly, a reload cartridge, and a reload cover. The jaw assembly comprises a reload support configured to receive the reload cartridge. The reload cover is releasably positionable on the reload cartridge. The reload cartridge comprises at least one protruding boss extending laterally outwardly therefrom. The reload cover comprises at least one snap feature extending therefrom, each snap feature engageable with a corresponding protruding boss. The at least one snap feature is not manually disengageable from the at least one protruding boss. Installation of the reload cartridge and reload cover to the reload support disengages the at least one snap feature from the at least one protruding boss.

In certain embodiments, a reload cartridge assembly for a surgical stapler is provided herein. The reload cartridge assembly comprises a cartridge body and a reload cover. The cartridge body has a generally elongate profile extending from a proximal end to a distal end. The cartridge body comprises an upper, tissue contacting surface and a pair of lateral surfaces. The upper, tissue contacting surface has a plurality of rows of staple pockets formed therein and at least one seating boss protruding upwards from the upper surface at the proximal end. The pair of lateral surfaces each comprise a protruding boss extending laterally outwardly at the distal end of the cartridge body. The reload cover is removably positionable on the upper surface. The reload cover has a generally planar configuration and a generally elongate profile extending from a proximal end to a distal end. The reload cover comprises a pair of latch arms extending downwardly from the distal end thereof. Each of the latch arms is engageable with a corresponding protruding boss to retain the reload cover to the upper surface of the cartridge body such that the reload cover is not manually removable.

In certain embodiments, a method of installing a reload cartridge to a reload support is provided herein. The surgical stapler comprises a jaw assembly comprising a reload support and the reload cartridge comprises a reload cover engaged thereto. The method comprises positioning a proximal end of the reload cartridge into a proximal end of the reload support. The method further comprises advancing a protruding boss adjacent the distal end of the reload cartridge into an engagement notch of the reload support such that the engagement notch releases a snap feature of the reload cover. The method further comprises removing the reload cover once the snap feature has been released.

DETAILED DESCRIPTION OF THE INVENTION

Figure 1:
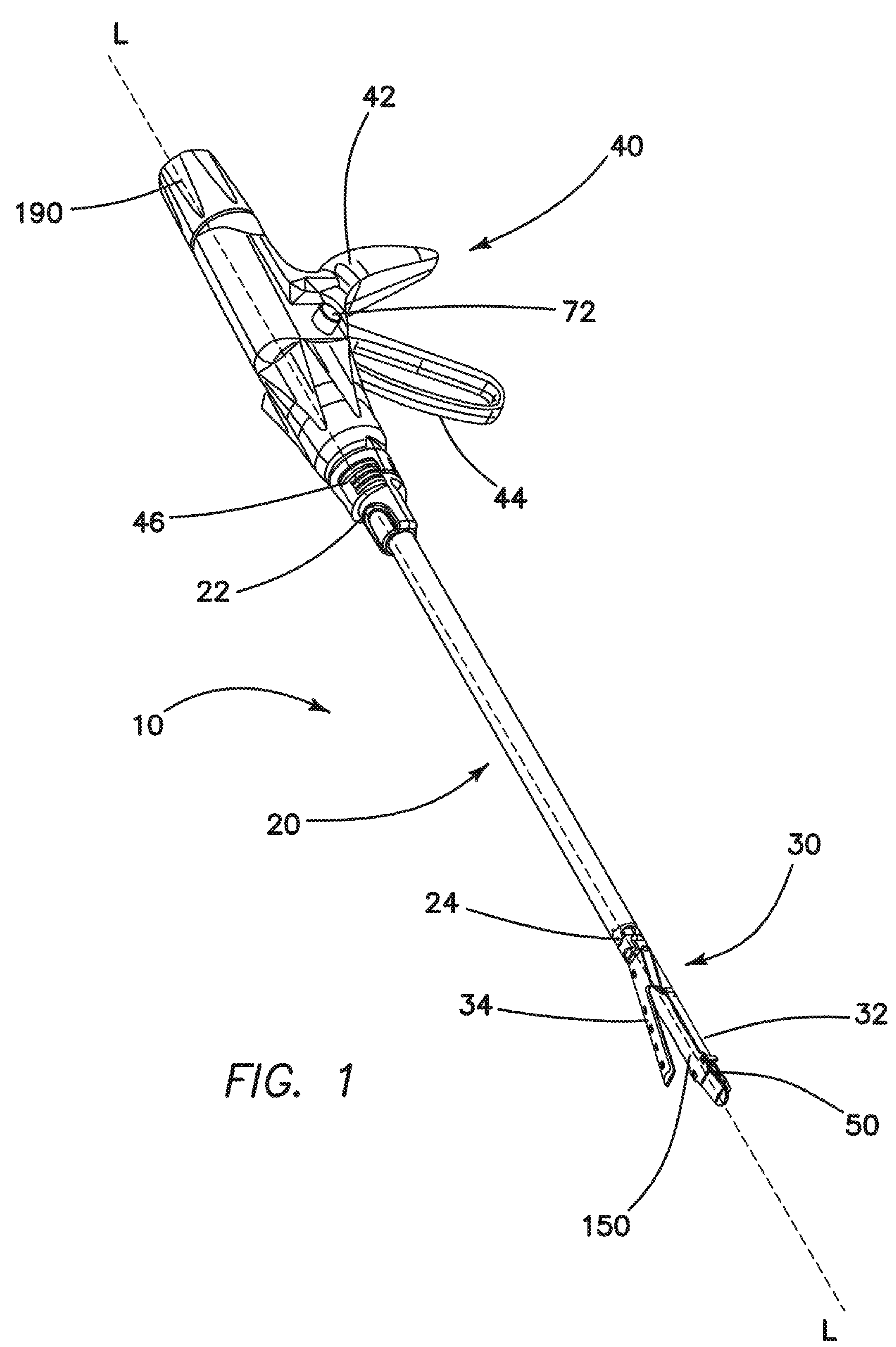
FIG. 1 is a perspective view of an embodiment of surgical stapling device with the jaws in an open configuration.
Figure 2:
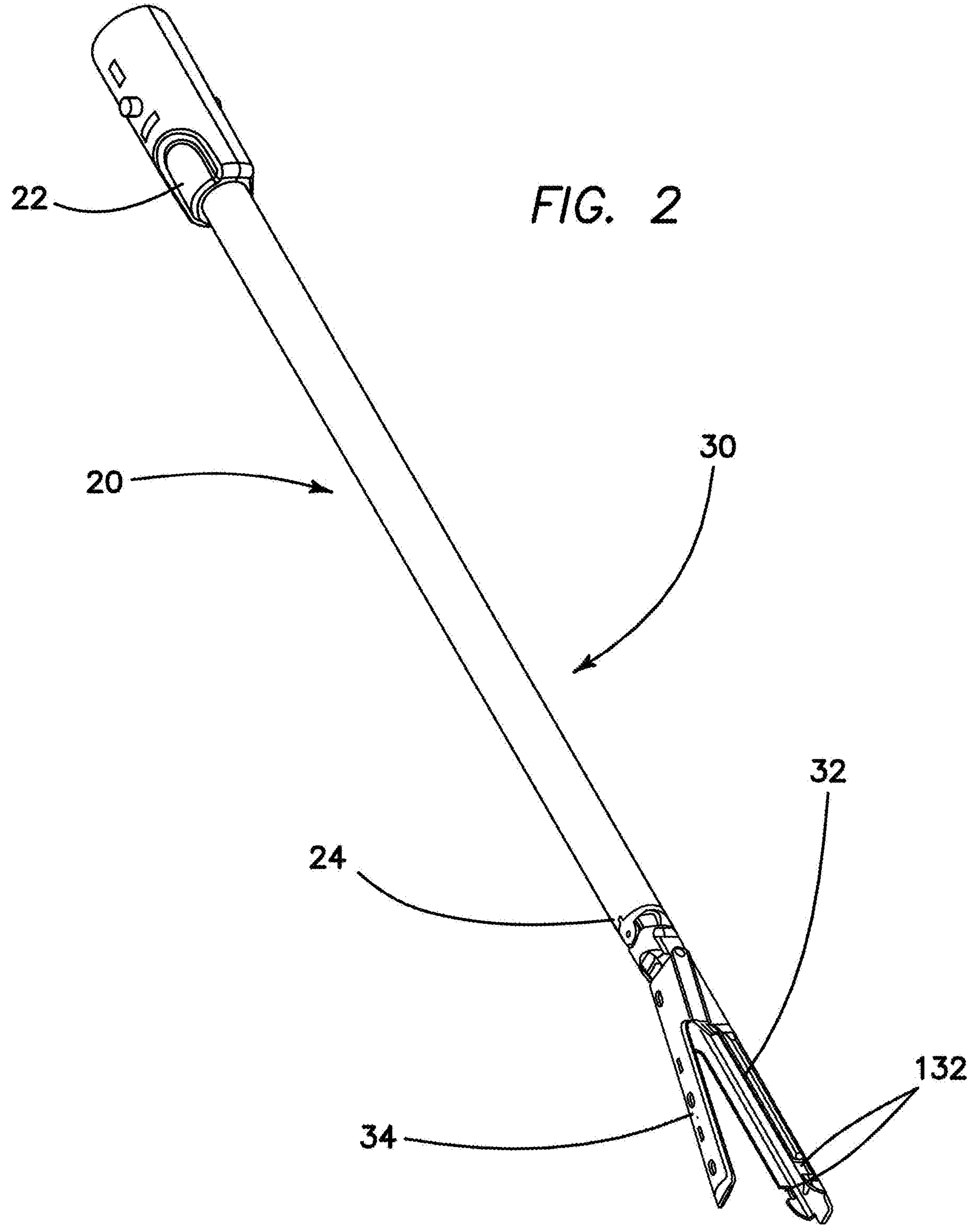
FIG. 2 is a perspective view of an embodiment of a reload shaft for the surgical stapling device of FIG. 1 with the jaws in an open configuration.

With reference to FIGS. 1-2, embodiments of surgical stapling device are illustrated. The embodiment of stapling device illustrated in FIGS. 1-3 includes a mechanical handle assembly 40, although various aspects of the reload cartridge and reload cover described herein can be used in conjunction with an electrically powered handle assembly. The illustrated embodiment of surgical stapler 10 comprises an elongate shaft 20, a jaw assembly 30, and a handle assembly 40. Various aspects of the elongate shaft 20 and jaw assembly 30 described herein can be used interchangeably with either the mechanical handle assembly 40 or a powered handle assembly. FIG. 1 illustrates the surgical stapler 10 with the jaw assembly 30 in an open configuration. FIG. 2 illustrates a removable reload shaft assembly comprising the elongate shaft 20 and jaw assembly 30 of the surgical stapler 10 with the jaw assembly 30 in an open configuration.

With continued reference to FIGS. 1 and 2, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIGS. 1 and 2, as illustrated, the elongate shaft 20 comprises a generally tubular member. The elongate shaft 20 extends from a proximal end 22 to a distal end 24. The elongate shaft 20 defines a central longitudinal axis, L. of the surgical stapler 10 extending between the proximal end 22 and the distal end 24. The jaw assembly 30 and reload cartridge 50 likewise have generally elongate configurations, each extending from respective a proximal end to a respective distal end, along the central longitudinal axis when aligned with the elongate shaft 20.

With continued reference to FIGS. 1 and 2, in the illustrated embodiment, the jaw assembly 30 is coupled to the elongate shaft 20 at the distal end 24 of the elongate shaft 20. The jaw assembly 30 comprises a first jaw 34 pivotally coupled to a second jaw 32. In the embodiment illustrated in FIGS. 1-2, the jaw assembly is articulably coupled to the elongate shaft such that the jaw assembly can be selectively positioned at an articulated position with respect to the central longitudinal axis L and an aligned position with respect to the central longitudinal axis L. The handle assembly of FIG. 1 includes an articulation knob 190 and articulation mechanism configured to provide continuously selectable articulation of a jaw assembly of an elongate shaft assembly through an articulation range. In an initial configuration, the second jaw 32 includes a plurality of staples positioned within a reload cartridge 50 positioned therein. Thus, the second jaw 32 defines a reload support.

With continued reference to FIGS. 1 and 2, in the illustrated embodiment, the jaw assembly 30 can be actuated from an open configuration (FIG. 1) to a closed configuration to a stapling configuration by an actuation member or beam that is longitudinally slidable within the elongate shaft. In an initial position, the beam can be positioned at the distal end 24 of the elongate shaft 20. With the beam in the initial position, the first jaw 34 is pivoted away from the second jaw 32 such that the jaw assembly 30 is in the open configuration. The second jaw 32 has an elongate configuration extending from the distal end of the elongate shaft. The actuation beam engages the first jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the second jaw 32 such that further translation of the actuation beam distally past the first distance deploys the plurality of staples 36 from the second jaw 32.

Figure 3:
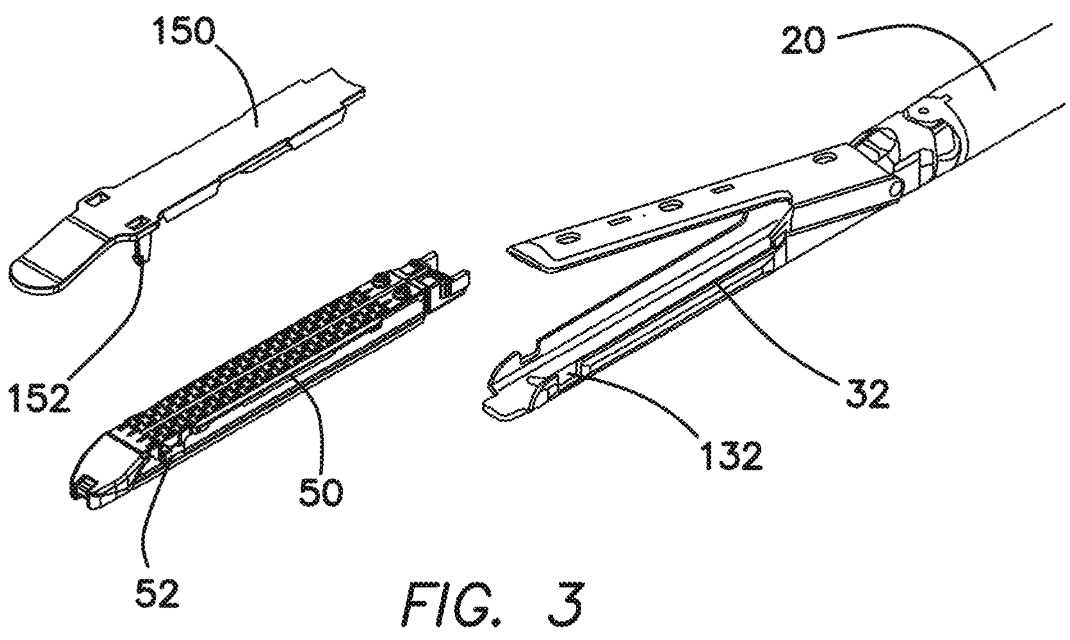
FIG. 3 is a partially exploded perspective view of a jaw assembly, reload cartridge, and reload cover of the surgical stapling device of FIG. 1.

With reference to FIGS. 1-3, in the illustrated embodiment, the handle assembly is coupled to the elongate shaft 20 at the proximal end 22 of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. The handle assembly 40 houses an actuation mechanism configured to selectively advance an actuation shaft responsive to movement of the movable handle 44 to actuate the actuation beam within the elongate a shaft a first distance in an open-close stroke to close the jaw assembly from an initial open position, a second distance beyond the first distance in a firing stroke to fire staples, and to return the actuation beam the second distance and the first distance to an initial position. In certain embodiments, a sliding selector 72 on the handle assembly can allow a user to select whether the handle assembly operates to actuate a jaw assembly in an open-close stroke or a firing stroke. Various embodiments of handle assemblies and associated actuation mechanisms are disclosed in U.S. Pat. No. 9,668,732, entitled "Surgical Stapler Handle Assembly Having Actuation Mechanism With Longitudinally Rotatable Shaft" and U.S. Patent application Ser. No. 15/485,620, filed Apr. 12, 2017, entitled "Surgical Stapler Having Articulation Mechanism," both of which are incorporated by reference herein in their entireties.

With continued reference to FIGS. 1-3, in some embodiments, the surgical stapler 10 can include the plurality of staples positioned in a disposable reload cartridge 50 while the handle assembly 40 and elongate shaft 20 are configured to be reused with multiple staple reload cartridges in a surgical procedure. The surgical stapler can include one or more grasping and firing lockout mechanisms that can limit functionality of the handle assembly to alert a user and enhance patient safety if no reload cartridge is present in the jaw assembly or if a partially or fully fired reload cartridge is present in the jaw assembly. In certain embodiments, a staple deployment member, such as a translatable sled or slider within the reload cartridge 50 can defeat one or more lockout mechanisms when the staple deployment member is in a proximal position in the jaw assembly, corresponding to an unfired reload cartridge is present in the surgical stapler 10.

With reference to FIG. 1, the handle assembly 40 includes a coupler 46 at the distal end thereof. The coupler 46 is adapted to engage the elongate shaft 20 of the surgical stapler 10. The coupler 46 can have a bayonet connection having an outer connector that can removably couple the handle assembly 40 to the elongate shaft 20, and an inner connector that can removably couple the actuation shaft of the handle assembly 42 to the actuation member of the elongate shaft 20. Accordingly, the surgical stapler 10 can be configured such that the handle assembly 40 can be reused with multiple disposable shafts and/or reload cartridges during a surgical procedure. It is contemplated that in other embodiments, the handle assembly and some portion of the elongate shaft can be reusable while a remainder of the elongate shaft and the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

As noted above, the elongate shaft, jaw assembly, reload cartridge, and reload covers described herein can also be used in conjunction with a powered stapler handle assembly. Various embodiments of powered handle assemblies and associated actuation mechanisms are disclosed in U.S. patent application Ser. No. 15/486,227, filed Apr. 12, 2017, entitled "Reload Shaft Assembly for Surgical Stapler;" U.S. patent application Ser. No. 15/486,008, filed Apr. 12, 2017, entitled "Surgical Stapler Having a Powered Handle;" and U.S. patent application Ser. No. 16/287,748, filed Feb. 27, 2019, entitled "Surgical Stapler Having a Powered Handle;" all of which are incorporated by reference herein in their entireties.

With reference to FIG. 3, a perspective view of the jaw assembly of the elongate shaft 20 is illustrated with the reload cartridge 50 and reload cover 150 removed from the second jaw 32. As illustrated, the reload cover 150 overlies the reload cartridge 50, and the reload cartridge 50 is positionable in the reload support defined by the second jaw 32. As further described herein, the reload cover 152 can include one or more snap features 152 engageable with a corresponding one or more protrusions or bosses 52 on the reload cartridge 50. The snap features 152 and bosses 52 are alignable with an engagement notch 132 or release recess formed in the second jaw 32 when the reload cartridge 50 is properly positioned and seated within the second jaw 32. In the illustrated embodiment, the reload cartridge 50 includes a plurality of staples disposed therein, each staple positioned in its own staple pocket formed through a body of the reload cartridge. In the illustrated embodiment, the staple pockets are arranged in a plurality of longitudinally extending rows. An upper surface of the reload cartridge 50 defines a tissue contact surface which, in certain embodiments, can be substantially planar. The reload cartridge further comprises a blade channel formed therein. As illustrated, the blade channel longitudinally extends between two adjacent rows of staple pockets such that translation of a cutting blade through the blade channel transects tissue between rows of staples that have been deployed into tissue positioned in the jaws when staples are fired.

Figure 4:
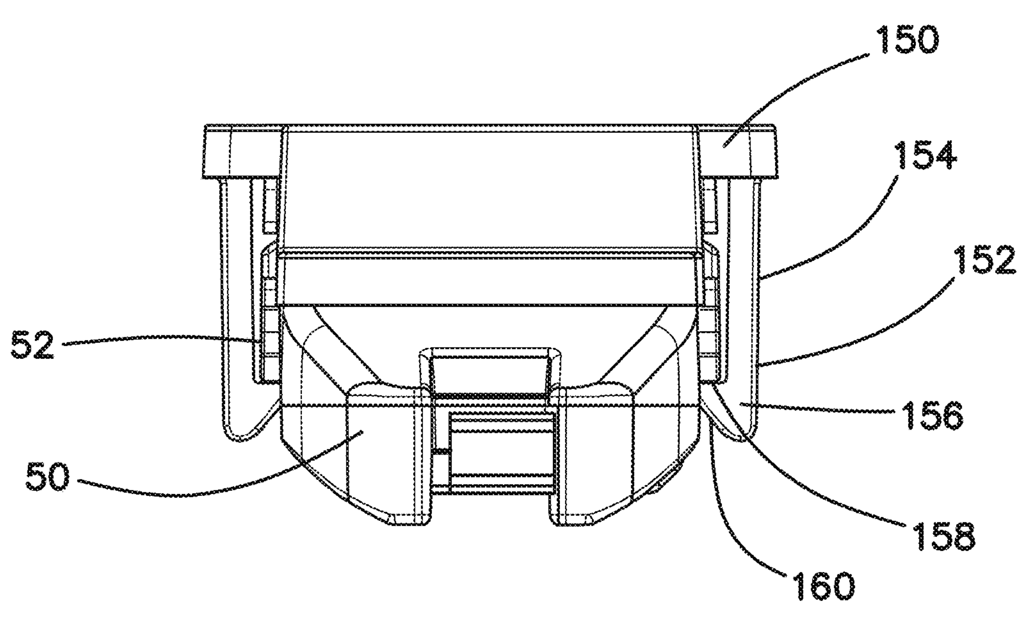
FIG. 4 is an end view of a reload cartridge and a reload cover of the surgical stapling device of FIG. 1.
Figure 5:
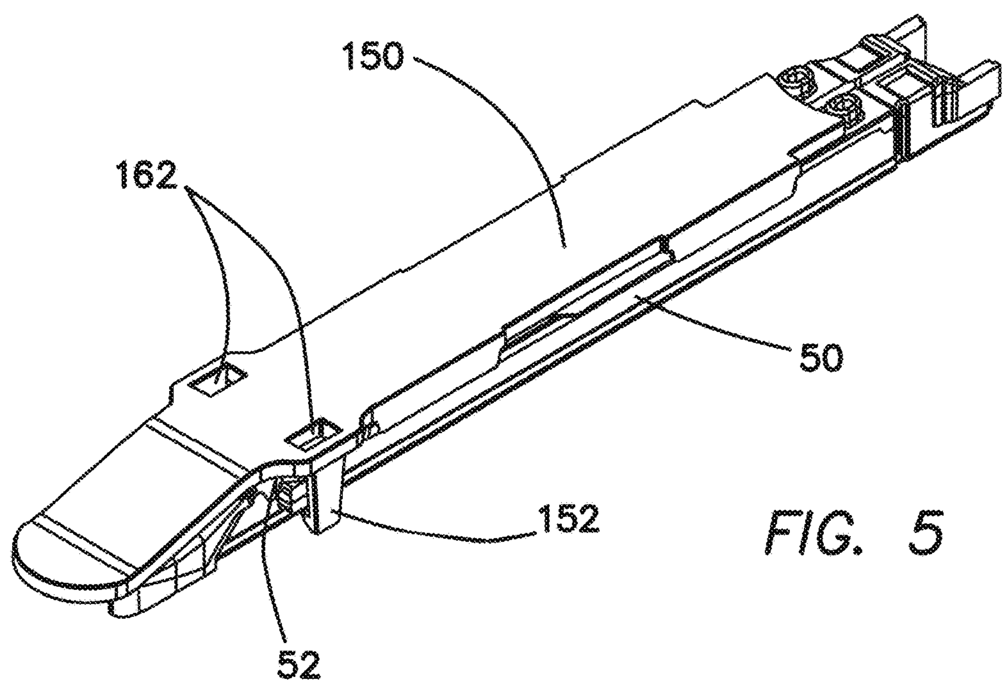
FIG. 5 is a perspective view of the reload cartridge and reload cover of FIG. 4.

With reference to FIGS. 4-5, views of the reload cartridge 50 and reload cover 150 engaged with the reload cartridge 50 are illustrated. As illustrated, the reload cover 150 is engaged with the reload cartridge 50 to abut, contact, or be spaced adjacent to the upper surface of the reload cartridge. Thus, the reload cover 150 can protect the tissue contact surface of the reload 50 from impacts which could cause marring or damage during shipping and transport of the reload cartridge 50. Desirably, with the reload cover 150 positioned directly on the upper surface of the reload cartridge 50, the plurality of staples are retained within the staple pockets in the reload cartridge 50. Thus, prior to and during installation of the reload cartridge in the jaw assembly, the plurality of staples are unlikely to be inadvertently dislodged from their unfired positions by any impacts or other vibratory forces during shipment or manipulation of the reload cartridge.

With continued reference to FIGS. 4-5, it can be desirable that the reload cover 150 is maintained on the reload cartridge in a manner that is not easily manually removable such that a user would be largely unable to remove the reload cover before installation in the jaw assembly. Advantageously, such an arrangement can require a user to properly position and install the reload cartridge in the jaw assembly before the reload cover can be removed. In the illustrated embodiment, the reload cover 150 can comprise at least one snap feature 152 configured to engage a corresponding at least one boss 52 protruding from the reload cartridge. In the illustrated embodiment, the reload cover 150 comprises two snap features 152 laterally outwardly positioned adjacent a distal end of the reload cover 150. In other embodiments, it is contemplated that a reload cover can comprise more than two snap features and/or can comprise snap features positioned adjacent the proximal end of the reload cover. Each snap feature comprises an arm 154 extending downwardly from a generally planar cover surface of the reload cover. The arm 154 comprises a latching tooth 156 positioned at an end thereof opposite the cover surface of the reload cover. The snap features 152 are flexible such that upon initial assembly with a reload cartridge, the snap features will flex laterally outwardly such that the latching tooth can be advanced over the boss 52 protruding laterally from the cartridge body of the reload cartridge. Desirably, in some embodiments, the arm 154 can be biased laterally inwardly, that is, towards a longitudinal centerline of the reload cover. In some embodiments, the arm 154 can extend in a direction slightly laterally inwardly such that the arm 154 is not joined to the cover surface of the reload cover at a perpendicular angle, but rather, the end of each arm is positioned laterally inwardly of the opposite end of the arm at the cover surface. Thus, in these embodiments when a reload cover 150 is positioned on a reload cartridge 50, each latching tooth 156 securely engages a lateral surface of the reload cartridge and is not readily manually removable.

With continued reference to FIGS. 4-5, the latching tooth 156 can extend laterally inwardly from the end of the arm member of the snap feature 152, and the latching tooth 156 can comprise a latch surface 158 on an upper side or surface thereof and a tapered edge 160 on a lower side thereof. The tapered edge 160 is configured with a transverse extent relative to the generally planar surface of the reload cover such that the tapered edge 160 can engage various features, such as the boss 52 of the reload cartridge 50 during initial assembly of the reload cover 150 to the reload cartridge 50, to flex the arm 154 laterally outwardly. The latch surface 158 can engage a lower, engagement surface of the boss 52 to maintain the reload cover 150 on the reload cartridge. During installation and proper fitting of the reload cartridge 50 and reload cover 150 assembly to a jaw assembly of a surgical stapler, the tapered edge 160 can engage the jaw assembly as further described below and illustrated in FIG. 6 to flex the snap feature 152 laterally outward such that the latch surface 158 disengages the lower, engagement surface of the boss 52 and the reload cover 150 is separated from the reload cartridge 50.

With reference to FIG. 5, an aperture 162 can be formed through the reload cover 150 adjacent each snap feature 152. Thus, in the illustrated embodiment each aperture 162 can be positioned at the distal end of the reload cover at a laterally outward position. As illustrated each snap feature 152 is positioned laterally outwardly of an aperture 162. In certain embodiments, the reload cover can have a generally rectangular profile sized to cover the plurality of rows of staple pockets on the reload cartridge, and the snap features can be disposed on lateral extensions or wings positioned laterally outwardly of the generally rectangular profile. An aperture 162 can be formed in each lateral extension. The aperture 162 can provide a locally flexible portion of the reload cover 150 to allow flexing of the snap feature 152 relative to the body of the reload cover 150. Additionally, the aperture 162 can allow a user to flex the snap features 152 to release the reload cover 150 from the reload cartridge 50 with a hand tool, such as a small screwdriver inserted through the aperture 162. Thus, while assembly of the reload cover 150 with the reload cartridge can be difficult to manually remove to prevent, for example, inadvertent uncovering of staple pockets, in certain instances the reload cover can be removed through the use of a hand tool.

Figure 6:
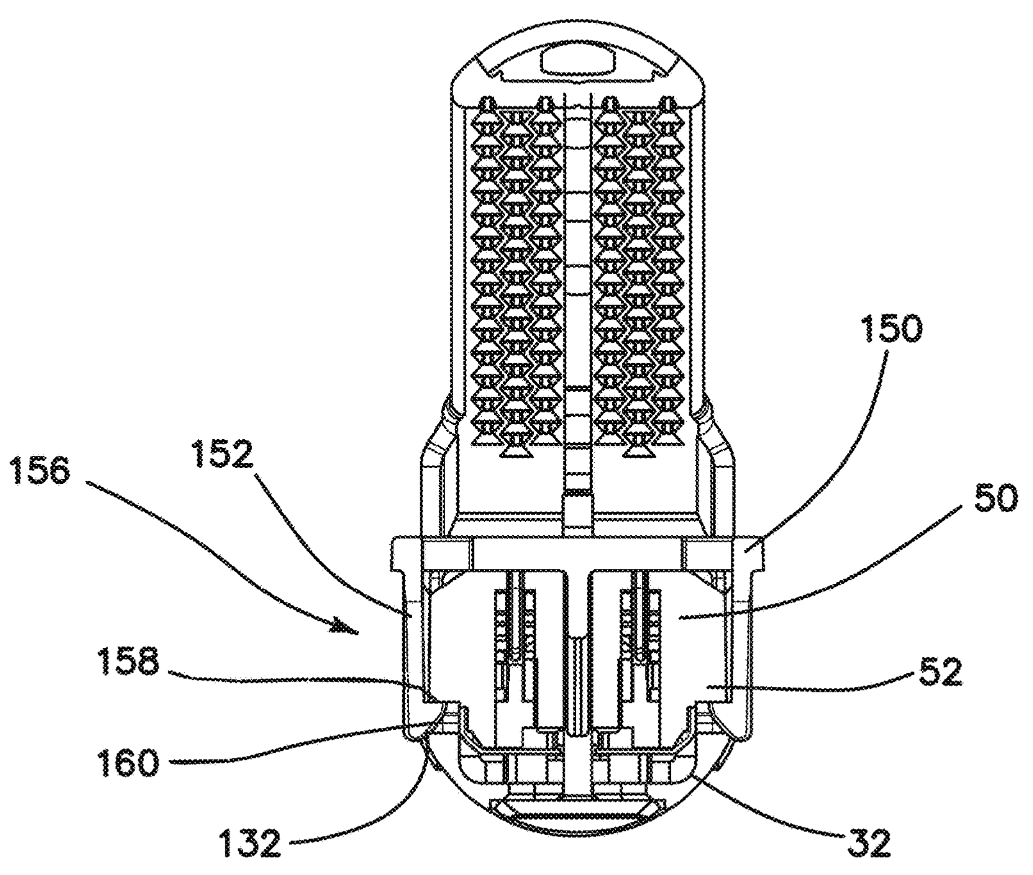
FIG. 6 is a cross-sectional end view of a jaw assembly with a partially installed reload cartridge and reload cover of the surgical stapling device of FIG. 1.

With reference to FIG. 6, a cross-sectional end view of the jaw assembly 30 of an embodiment of surgical stapler is illustrated. As illustrated, the reload cartridge 50 and reload cover 150 have been positioned in the second jaw 32 and partially installed. To position the reload cartridge 50 in the reload support of the second jaw 32, a user initially positions a proximal end of the reload cartridge 50 in the reload support at the proximal end. The user then pivots the distal end of the reload cartridge downwardly onto the distal end of the reload support. The reload support of the second jaw 32 can comprise a channel sized and configured to receive a reload cartridge. The reload support comprises at least one engagement notch 132 or release recess corresponding to the at least one boss 52 and snap feature 152. As the reload cartridge 50 is properly positioned in the reload support such that the boss 52 on the cartridge body seats in the engagement notch 132 of the reload support, the tapered edge 160 of the latching tooth 156 of the snap feature 152 engages a surface of the engagement notch 132. In certain embodiments, the engagement notch 132 can be radiused or tapered to facilitate engagement with the latching tooth 156. Thus, with the reload cartridge 50 properly positioned in the reload support, the snap feature 152 is flexed laterally outwardly such that the latch surface 158 of the latching tooth 156 is disengaged from the boss 52, allowing removal of the reload cover 150. Moreover, as the distal end of the reload cartridge is seated in the reload support, the reload cover 150 is separated from the reload cartridge. FIG. 6 illustrates an initial engagement of the tapered edge 160 with the engagement notch 132 such that further downward movement of the reload cartridge 50 and reload cover 150 relative to the reload support would further flex the snap features 152. Thus, desirably, the tissue contact surface of the reload cartridge 50 can not easily be uncovered for use until the reload cartridge is properly positioned in the reload support of the jaw assembly 30. Failure to properly install reload cartridges within surgical staplers can lead to an incomplete or malformed staple line. Once a reload cartridge is installed to the reload support and the reload cover separated and removed from the reload cartridge, a user can complete a staple firing operation. Then the fired reload cartridge can be removed from the reload support and a second reload cartridge assembly comprising a reload cartridge and a reload cover can be inserted to the reload support as described above for use in a subsequent firing operation.

Figure 7:
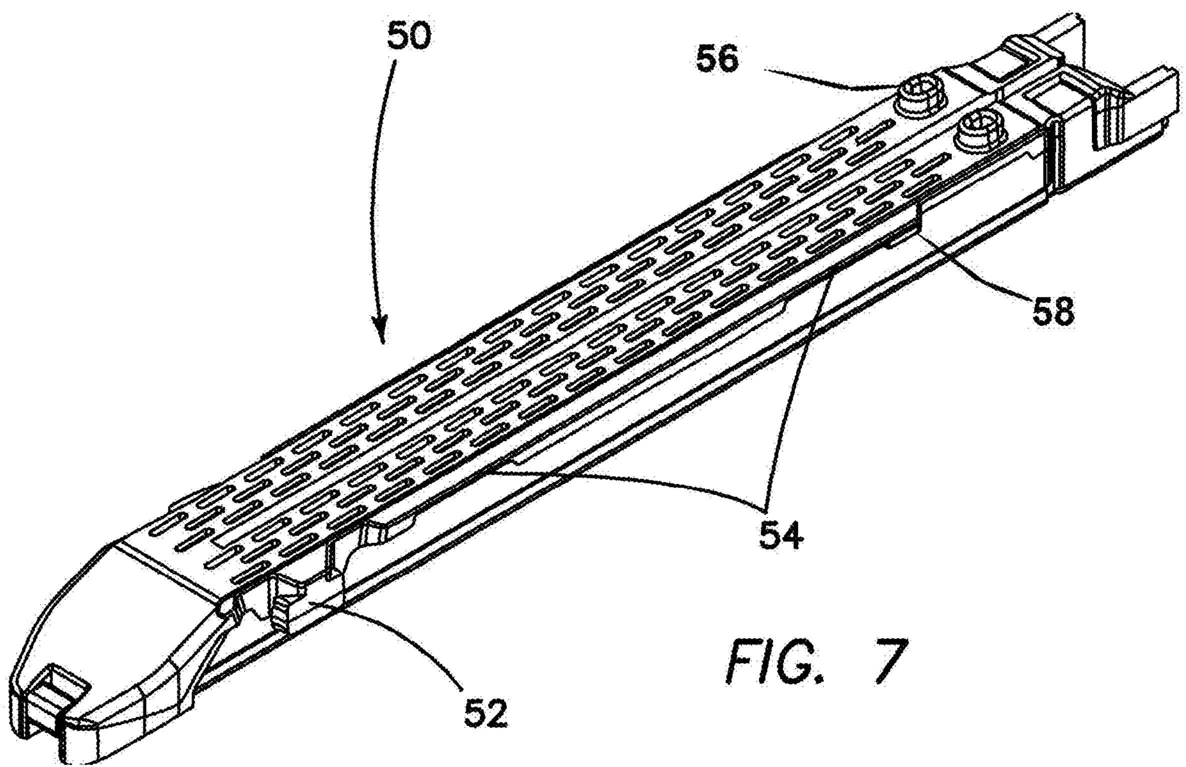
FIG. 7 is a perspective view of a reload cartridge of the surgical stapling device of FIG. 1.
Figure 8:
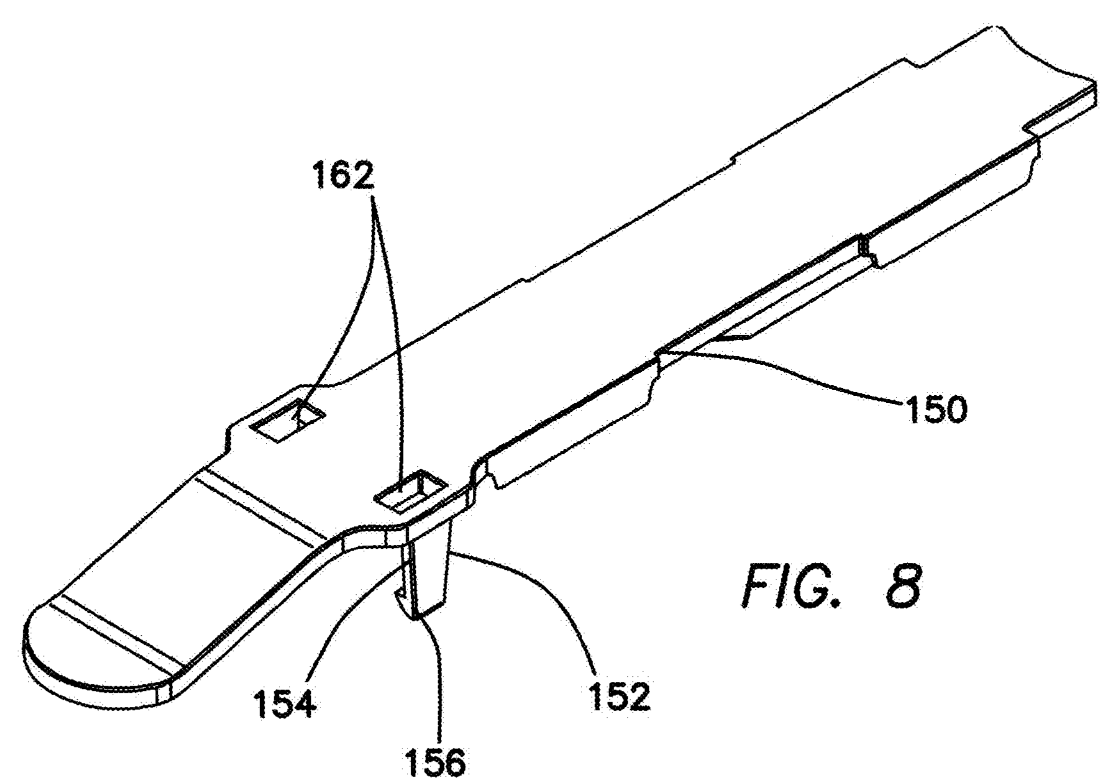
FIG. 8 is a perspective view of a reload cover of the surgical stapling device of FIG. 1.

With reference to FIG. 7, a perspective view of the reload cartridge 50 of an embodiment of surgical stapler is illustrated. As illustrated the reload cartridge 50 has a generally elongate profile extending from a proximal end to a distal end. The reload cartridge 50 comprises an upper, tissue contacting surface and a pair of lateral surfaces. The upper surface of the reload cartridge 50 can include a plurality of longitudinally extending rows of staple pockets having a blade channel extending therebetween. In the illustrated embodiment, the upper surface can further comprise at least one seating boss 56 protruding upwardly from the proximal end of the reload cartridge 50. The seating boss 56 can facilitate maintenance of a desired spacing between jaws of the jaw assembly and seating of the reload cartridge when the stapler is closed and fired. As illustrated, the reload cartridge further comprises protruding bosses 52 extending laterally outwardly from the lateral surfaces adjacent a distal end of the reload cartridge 50. The reload cartridge 50 can also comprise at least one notch 54 or recess formed on a laterally protruding rail 58 at a location proximal the bosses 52. In the illustrated embodiment, the reload cartridge is substantially symmetric about the central longitudinal axis and each lateral surface includes a protruding boss 52 and laterally protruding rail 58.

With reference to FIGS. 8-12, various views of an embodiment of reload cover 150 of an embodiment of surgical stapler are illustrated. As illustrated, the reload cover 150 comprises a body having a generally planar configuration with a first surface configured to abut, contact, or be positioned adjacent the upper surface of a reload cartridge. The body of the reload cover can have an elongate configuration with a generally rectangular profile sized to cover the plurality or rows of staple pockets of a reload cover. A proximal end of the body of the reload cover can be sized and configured to contact or abut a seating boss at a proximal end of a reload cartridge. The body further comprises a second surface opposite the first surface. The reload cover comprises a tongue extending distally from the generally planar surface of the body. In the illustrated embodiment, the tongue can extend distally along a plane transverse to the plane defined by the generally planar surface of the body. The tongue can be configured to overlie a distal tapered end of the reload cartridge and extend further distally to a user-graspable distal tip.

With continued reference to FIGS. 8-12, the reload cover 150 comprises at least one snap feature 152 engageable with a boss on a reload cartridge and releasable upon installation in a jaw assembly. As illustrated, the reload cover 150 comprises a pair of snap features 152 extending transversely to the generally planar body adjacent opposite lateral edges at a distal end thereof. In the illustrated embodiments, the snap features 152 each include an arm 154 having a latching tooth 156 with a latch surface 158 and a tapered edge 160. The reload cover can further comprise apertures 162 formed adjacent the snap features 152.

Figures 9, 10:
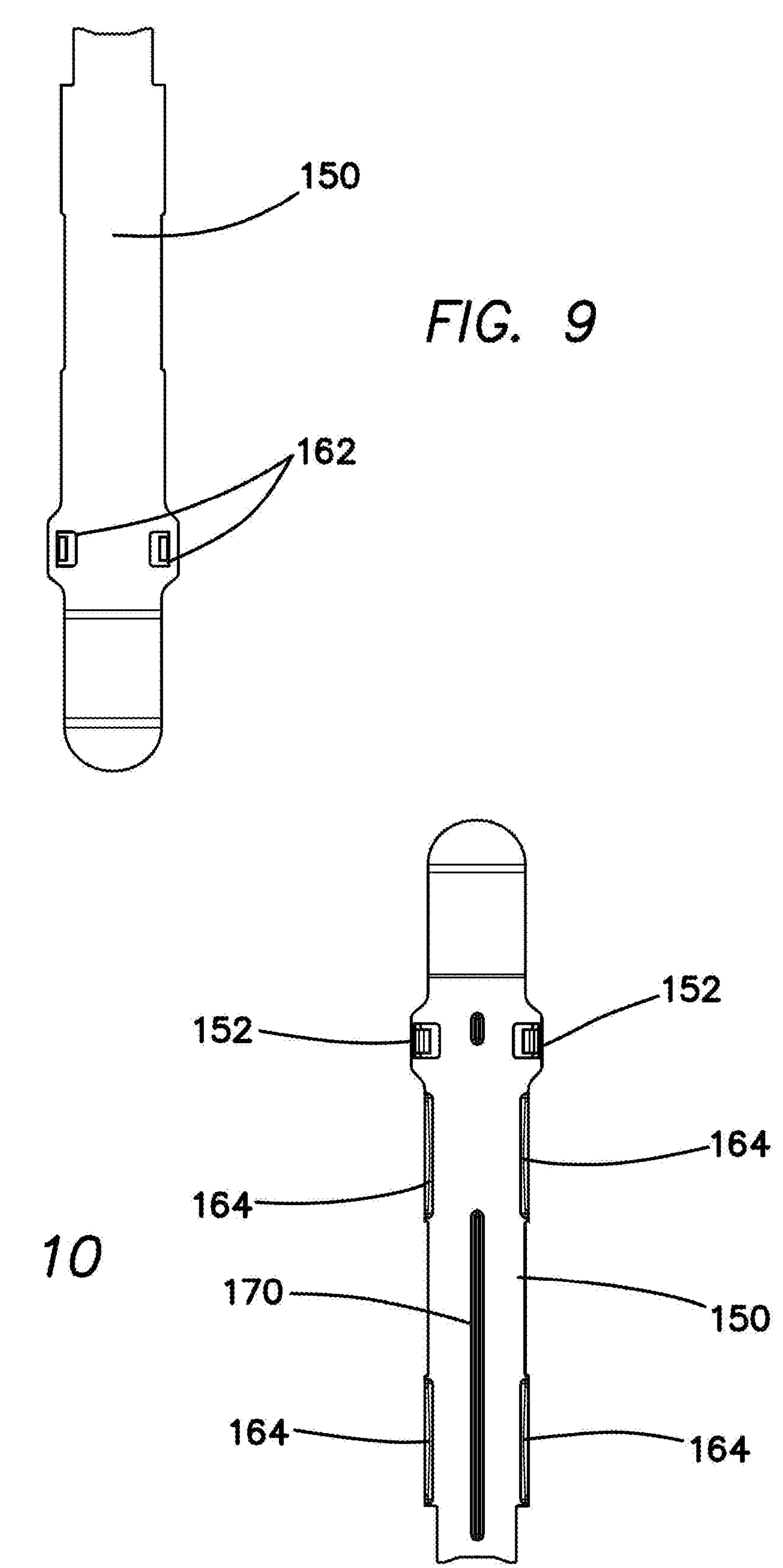
FIG. 9 is a top view of the reload cover of FIG. 8.
FIG. 10 is a bottom view of the reload cover of FIG. 8.
Figure 11:
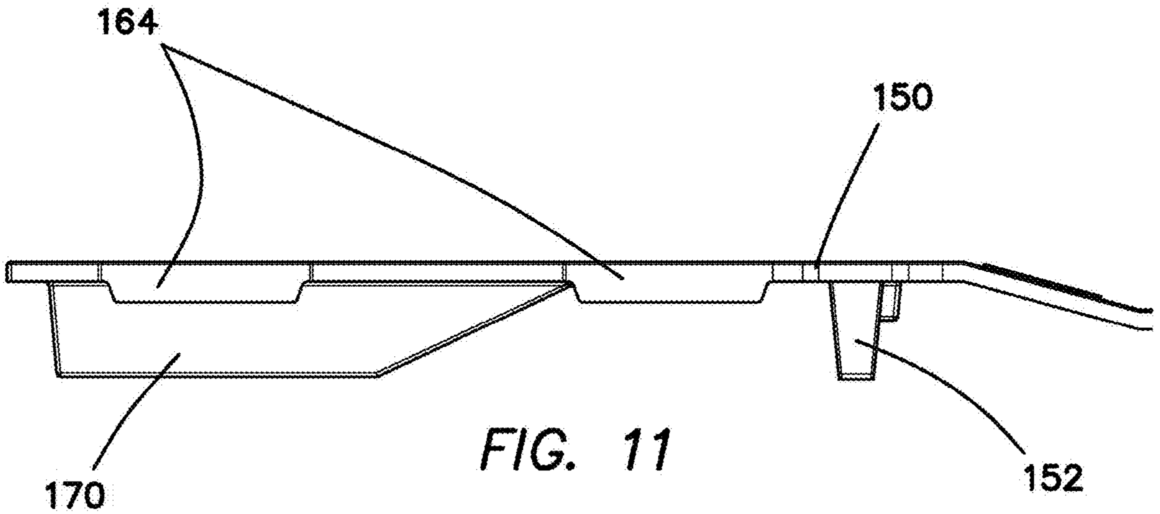
FIG. 11 is a side view of the reload cover of FIG. 8.
Figure 12:
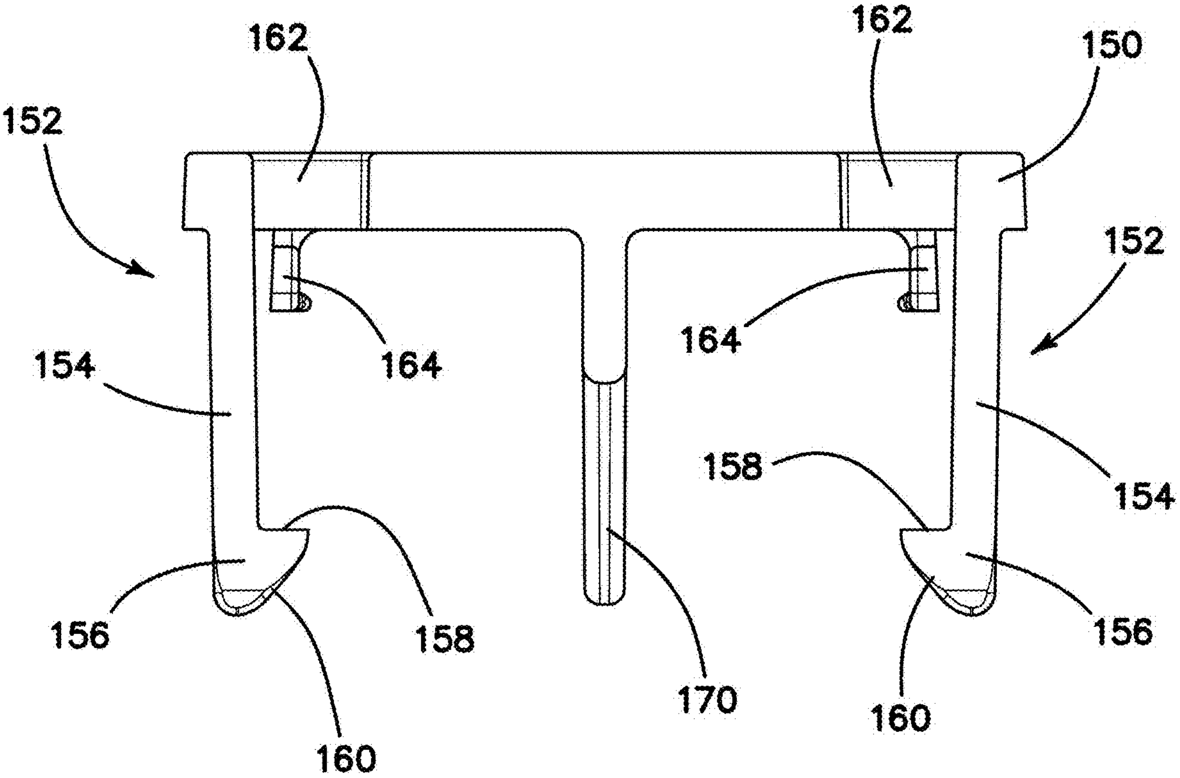
FIG. 12 is a cross-sectional end view of the reload cover of FIG. 8.

With reference to FIGS. 10-12, in certain embodiments, the reload cover can comprise one or more guide tabs or retention tabs 164 positioned along lateral edges of the body of the reload cover 150 proximal the snap features 152. The retention tabs 164 can be positioned to engage the notches 54 on the laterally extending rails of the reload cartridge (FIG. 7) to facilitate positioning and retention of the reload cover 150 on the reload cartridge 50. In certain embodiments, the guide tabs or retention tabs can each comprise a tip member such as a bulbous edge or a laterally inwardly extending flange configured to engage the recesses or notches 54 on the rails of the reload cartridge in a snap fit coupling. In the illustrated embodiment, the reload cover comprises a pair of distal retention tabs 164 positioned adjacent to and proximal to the snap features 152 and a pair of proximal retention tabs 164 positioned adjacent the proximal end of the reload cover 150 and proximal the distal retention tabs. In other embodiments, the reload cover can include more or fewer retention tabs such as, for example one pair of retention tabs or three pairs of retention tabs.

With reference to FIGS. 11-12, in certain embodiments, the reload cover 150 can comprise a fin 170 or alignment fin extending downwardly from the first surface of the reload cover 150 and positioned to be disposed in the blade channel of the reload cartridge. In the illustrated embodiment, the fin 170 has an elongate configuration, such that it can extend longitudinally within the blade channel to maintain a longitudinally aligned orientation of the reload cover with respect to the reload cartridge. In other embodiments, the fin 170 can have a reduced length and can comprise a post or arm positionable in the blade channel of the reload cartridge. The fin 170 can be positioned such that a proximal end of the fin 170 prevents distal movement of a staple deployment mechanism such as a sled or slider within the reload cartridge when the reload cover 150 is positioned on the reload cartridge 50. Thus, desirably, the fin 170 of the reload cover can prevent distal migration of a staple deployment mechanism prior to installation of the reload cartridge in the jaw assembly. If the staple deployment mechanism or slider were to distally translate prior to installation of the reload cartridge 50, in certain instances even an unfired cartridge would not defeat various fired reload lockout mechanisms which can be included in a stapling assembly. In certain embodiments, a fired reload lockout mechanism can comprise a lockout lever positioned adjacent a firing member of the stapler, and the fin 170 can maintain the staple deployment mechanism in a position to engage the lockout lever. Thus, desirably, the reload cover 150 can prevent inadvertent operation of a fired reload lockout mechanism of a stapler by an unfired reload cartridge.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A surgical stapling device comprising:

an elongate shaft;

a reload cartridge having a proximal end and a distal end and extending longitudinally from the proximal end to the distal end, the reload cartridge comprising at least one protruding boss extending laterally outwardly therefrom at the distal end;

a jaw assembly, the jaw assembly comprising a reload support configured to receive the reload cartridge; and a reload cover having a proximal end and a distal end and extending longitudinally from the proximal end to the distal end, the reload cover releasably positionable on the reload cartridge, the reload cover comprising at least one latch arm extending therefrom at the distal end and a corresponding at least one aperture adjacent the at least one latch arm, each latch arm engageable with a corresponding protruding boss;

wherein the reload cover is removable from the reload cartridge upon one of:

installation of the reload cartridge and reload cover to the reload support to disengage the at least one latch arm from the at least one protruding boss, and insertion of a tool through the at least one aperture to selectively disengage the at least one latch arm from the at least one protruding boss;

wherein the reload support comprises at least one engagement notch formed therein positioned to engage the at least one latch arm when the reload cartridge and the reload cover are installed in the reload support;

wherein the at least one latch arm comprises an arm member extending from the reload cover to an end, and a latch tooth extending laterally inwardly from the arm member at the end; and wherein the latch tooth has a release surface positioned to engage the engagement notch to displace the latch tooth laterally outwardly upon installation of the reload cartridge to the reload support.

2. The surgical stapling device of claim 1, wherein each of the at least one latch arms is biased laterally inwardly.

3. The surgical stapling device of claim 2, wherein each of the at least one latch arms extends in a direction laterally inwardly.

4. The surgical stapling device of claim 1, wherein the latch tooth has a lower side and wherein the release surface comprises a tapered edge on the lower side.

5. The surgical stapling device of claim 1, wherein the latch tooth has an upper side and wherein the latch tooth comprises a latch surface on the upper side thereof.

6. The surgical stapling device of claim 5, wherein the at least one protruding boss has a lower surface, and wherein the latch surface of the latch tooth engages the lower surface of the protruding boss when the reload cover is positioned on the reload cartridge.

7. The surgical stapling device of claim 1, wherein the reload cartridge comprises a blade channel and wherein the reload cover comprises a fin positionable within the blade channel when the reload cover is positioned on the reload cartridge.

8. The surgical stapling device of claim 1, wherein each of the at least one latch arm is positioned laterally outwardly of a corresponding one of the at least one aperture.

9. The surgical stapling device of claim 8, wherein the reload cover comprises a rectangular profile and further comprises at least one lateral extension positioned laterally outwardly of the rectangular profile and wherein each of the at least one latch arm extends from a corresponding one of the at least one lateral extension.

10. The surgical stapling device of claim 9, wherein each of the at least one apertures is formed in a corresponding one of the at least one lateral extension.

11. A reload cartridge assembly for a surgical stapler, the reload cartridge assembly comprising:

a cartridge body having a generally elongate profile extending from a proximal end to a distal end, and the cartridge body comprising:

an upper surface having a plurality of rows of staple pockets formed therein and a blade channel extending between two adjacent rows of the plurality of rows of staple pockets; and a pair of lateral surfaces, the pair of lateral surfaces each comprising a protruding boss extending laterally outwardly at the distal end of the cartridge body; and a reload cover removably positionable on the upper surface, the reload cover having a generally rectangular profile and a generally elongate profile extending from a proximal end to a distal end; the reload cover comprising:

a pair of lateral extensions positioned laterally outwardly of the rectangular profile at the distal end of the reload cover;

a pair of latch arms each extending downwardly and laterally inwardly from a corresponding one of the pair of lateral extensions; and a pair of apertures through the reload cover, each aperture positioned adjacent to a corresponding one of the pair of latch arms;

wherein each of the latch arms is engageable with a corresponding protruding boss to retain the reload cover to the upper surface of the cartridge body;

wherein each latch arm of the pair of latch arms comprises an arm member extending from the reload cover to an end, and a latch tooth extending laterally inwardly from the arm member at the end; and wherein the latch tooth has a release surface configured to displace the latch tooth laterally outwardly upon installation of the reload cartridge to the surgical stapler.

12. The reload cartridge assembly of claim 11, wherein the latch tooth has a lower side and wherein the release surface comprises a tapered edge on the lower side.

13. The reload cartridge assembly of claim 11, wherein the latch tooth has an upper side and wherein the latch tooth comprises a latch surface on the upper side thereof.

14. The reload cartridge assembly of claim 13, wherein the protruding boss has a lower surface, and wherein the latch surface of the latch tooth engages the lower surface of the protruding boss when the reload cover is positioned on the reload cartridge.

15. The reload cartridge assembly of claim 11, wherein the reload cover comprises a fin positionable within the blade channel when the reload cover is positioned on the reload cartridge.

* * * * *